US012693263B2

(12) United States Patent
Liu et al.

(10) Patent No.: US 12,693,263 B2
(45) Date of Patent: Jul. 28, 2026

(54) MOLDED FLOW CHANNEL

(71) Applicant: Roche Sequencing Solutions, Inc.,
Pleasanton, CA (US)

(72) Inventors: Edward Liu, Saratoga, CA (US);
Kenneth M. Stothers, San Jose, CA
(US); Markus Wallgren, Los Altos
Hills, CA (US); Janusz B. Wojtowicz,
Sunnyvale, CA (US); Robert A. Yuan,
San Jose, CA (US)

(73) Assignee: Roche Sequencing Solutions, Inc.,
Pleasanton, CA (US)

( * ) Notice: Subject to any disclaimer, the term of this
patent is extended or adjusted under 35
U.S.C. 154(b) by 0 days.

(21) Appl. No.: 19/364,124

(22) Filed: Oct. 21, 2025

(65) Prior Publication Data

US 2026/0043769 A1 Feb. 12, 2026

Related U.S. Application Data

(63) Continuation of application No. 19/218,047, filed on
May 23, 2025, now Pat. No. 12,467,899, which is a
continuation of application No. 18/316,920, filed on
May 12, 2023, now Pat. No. 12,313,588, which is a
continuation of application No. 16/947,043, filed on
Jul. 15, 2020, now Pat. No. 11,686,706, which is a
continuation of application No. 15/410,586, filed on
Jan. 19, 2017, now Pat. No. 10,718,737.

(60) Provisional application No. 62/286,826, filed on Jan.
25, 2016, provisional application No. 62/281,662,
filed on Jan. 21, 2016, provisional application No.
62/281,663, filed on Jan. 21, 2016.

(51) Int. Cl.
*G01N 27/447* (2006.01)
*G01N 33/487* (2006.01)

(52) U.S. Cl.
CPC . *G01N 27/44791* (2013.01); *G01N 33/48721*
(2013.01)

(58) Field of Classification Search
None
See application file for complete search history.

(56) References Cited

U.S. PATENT DOCUMENTS

2014/0174927 A1* 6/2014 Bashir .................. G01N 27/447
204/603

OTHER PUBLICATIONS

Rollings, et al., "Chapter 5: DNA Characterization with Ion Beam-
Sculpted Silicon Nitride Nanopores" in Nanopore-Based Technol-
ogy, pp. 79-97, Method in Molecular Biology, vol. 870, Humana
Press (Year: 2012).*
A.R. Hall, et al., "Hybrid pore formation by directed insertion of
α-haemolysin into solid-state nanopores", Nature Nanotechnology
5(12): p. 874-877, Dec. 2010.*

* cited by examiner

*Primary Examiner* — J. Christopher Ball

(74) *Attorney, Agent, or Firm* — Winston Chu

(57) ABSTRACT

A nanopore based sequencing system includes a plurality of
nanopore sensors. Each nanopore sensor has a portion for
receiving a fluid. The nanopore based sequencing system
includes a fluid chamber configured to guide the fluid over
the plurality of nanopore sensors and an inlet configured to
deliver the fluid into the fluid chamber. At least a portion of
the fluid chamber is made of a material that has been molded
around at least a portion of an electrode.

18 Claims, 30 Drawing Sheets

702

FLUID
REMNANT

702

MOLDED FLOW CHANNEL

CROSS REFERENCE TO OTHER APPLICATIONS

This application is a continuation of U.S. patent application Ser. No. 19/218,047, filed May 23, 2025, which is a continuation of U.S. patent application Ser. No. 18/316,920, filed May 12, 2023, now U.S. Pat. No. 12,313,588, which is a continuation of U.S. patent application Ser. No. 16/947, 043, filed Jul. 15, 2020, now U.S. Pat. No. 11,686,706, which is a continuation of U.S. patent application Ser. No. 15/410,586, filed Jan. 19, 2017, now U.S. Pat. No. 10,718, 737, entitled MOLDED FLOW CHANNEL, which claims priority to U.S. Provisional Ser. No. 62/281,663 entitled CHIP PERIMETER SEAL AND BOND filed Jan. 21, 2016, and claims priority to U.S. Provisional Ser. No. 62/281,662 entitled USE OF TITANIUM NITRIDE AS AN INTERME-DIATE LAYER IN BONDING GLASS TO A SILICON CHIP filed Jan. 21, 2016, and claims priority to U.S. Provisional Ser. No. 62/286,826 entitled USE OF TITA-NIUM NITRIDE AS AN INTERMEDIATE LAYER IN BONDING GLASS TO A SILICON CHIP filed Jan. 25, 2016, all of which are incorporated herein by reference for all purposes.

BACKGROUND OF THE INVENTION

Advances in micro-miniaturization within the semicon-ductor industry in recent years have enabled biotechnolo-gists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying draw-ings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
FIG. 1 illustrates an embodiment of a cell 100 in a nanopore based sequencing chip.
Figure 1:
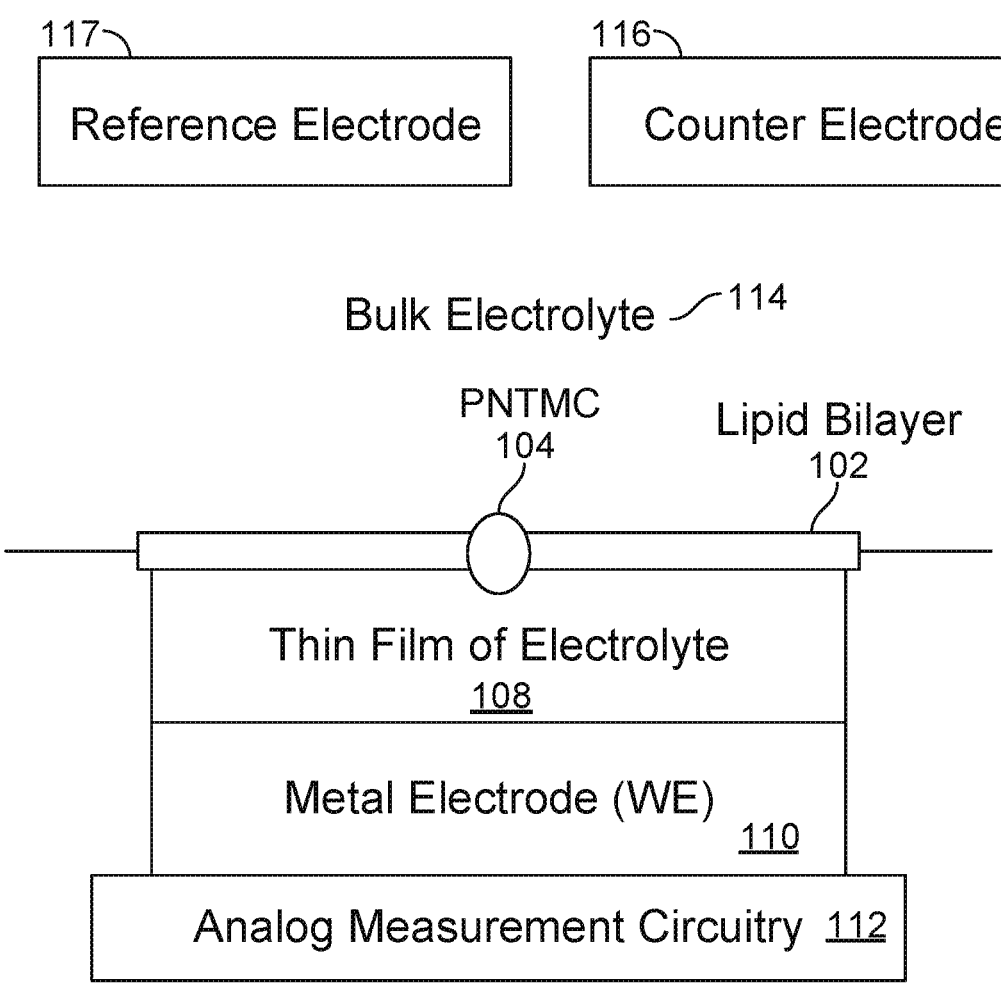

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor. The cell also includes a reference electrode 117.

Figure 2:
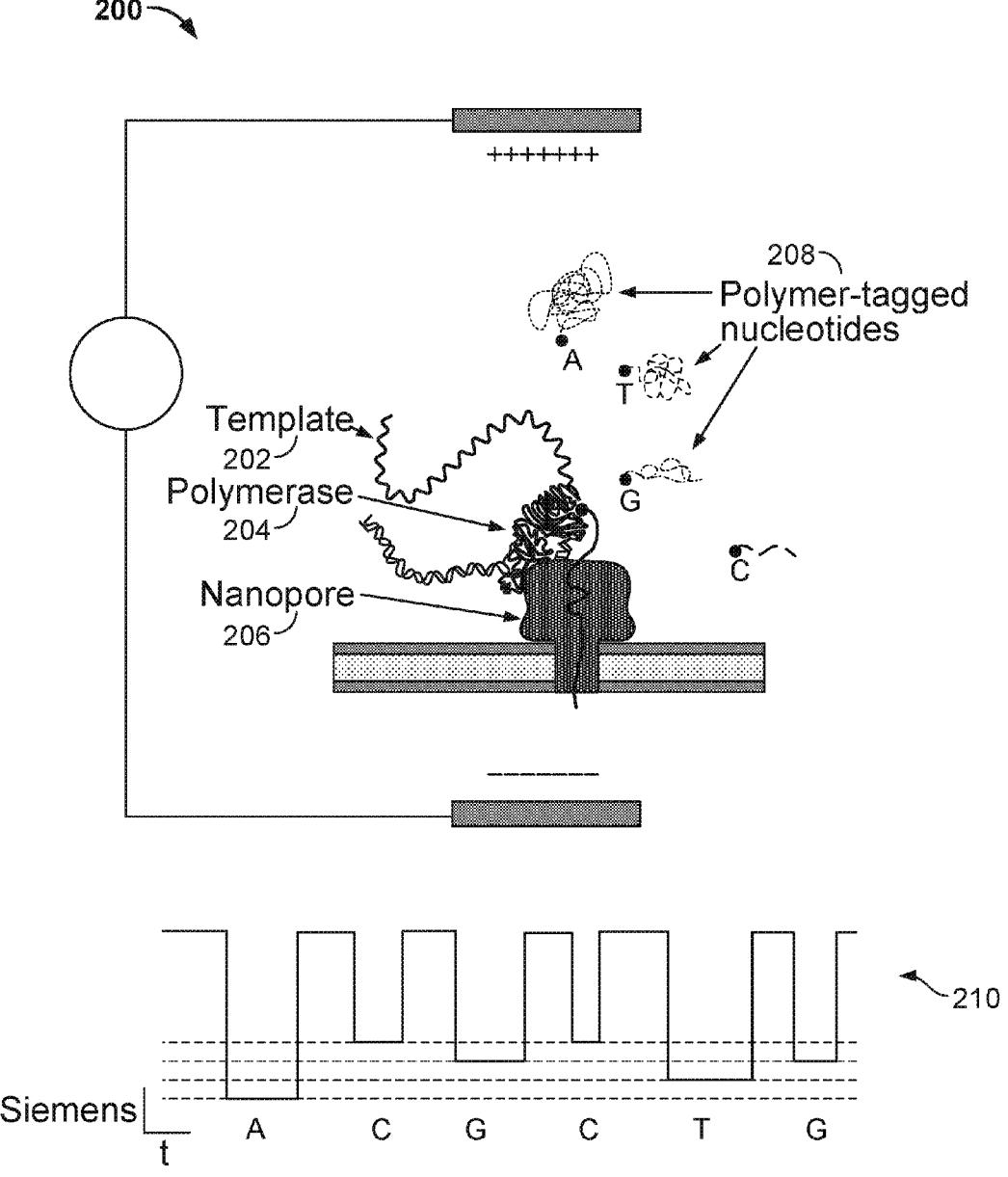
FIG. 2 illustrates an embodiment of a cell 200 performing nucleotide sequencing with the Nano-SBS technique.

In some embodiments, a nanopore array enables parallel sequencing using the single molecule nanopore based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
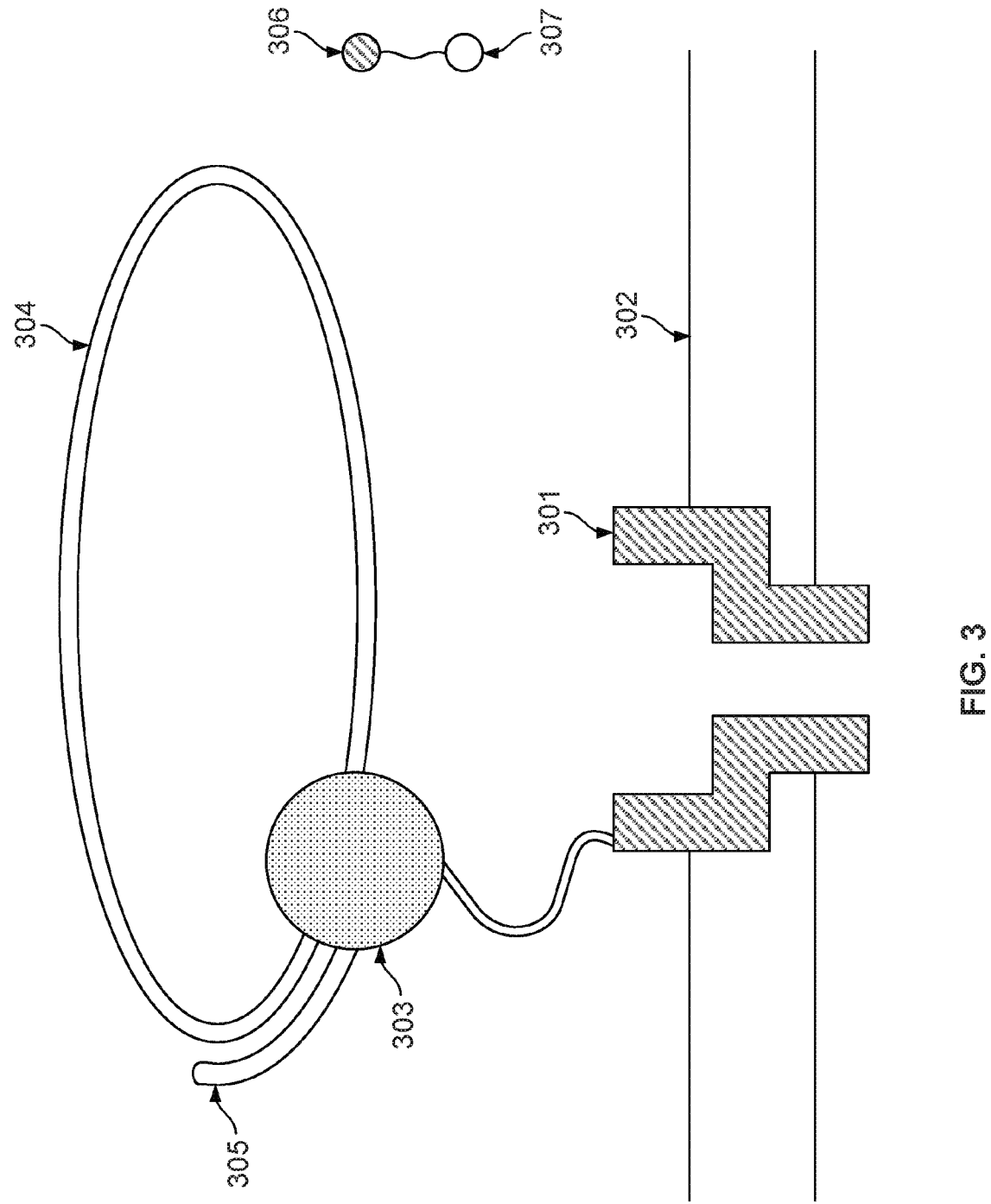
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
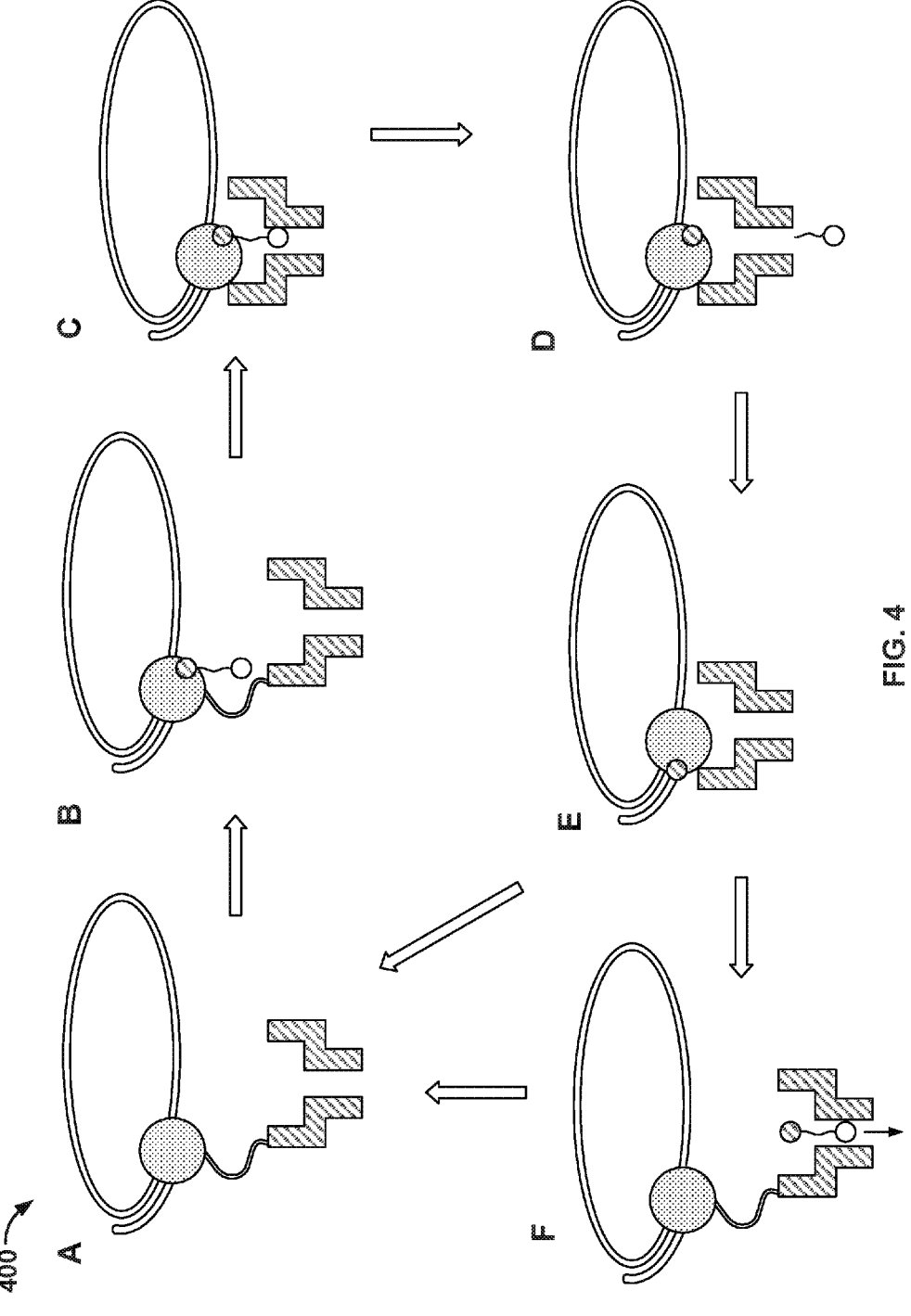
FIG. 4 illustrates an embodiment of a process 400 for nucleic acid sequencing with pre-loaded tags.

FIG. 4 illustrates an embodiment of a process 400 for nucleic acid sequencing with pre-loaded tags. At stage A, a tagged nucleotide (one of four different types: A, T, G, or C) is not associated with the polymerase. At stage B, a tagged nucleotide is associated with the polymerase. At stage C, the polymerase is in close proximity to the nanopore. The tag is pulled into the nanopore by an electrical field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage B.

Before the polymerase is docked to the nanopore, the conductance of the nanopore is ~300 pico Siemens (300 pS). At stage C, the conductance of the nanopore is about 60 pS, 80 pS, 100 pS, or 120 pS corresponding to one of the four types of tagged nucleotides.

The polymerase undergoes an isomerization and a trans-phosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
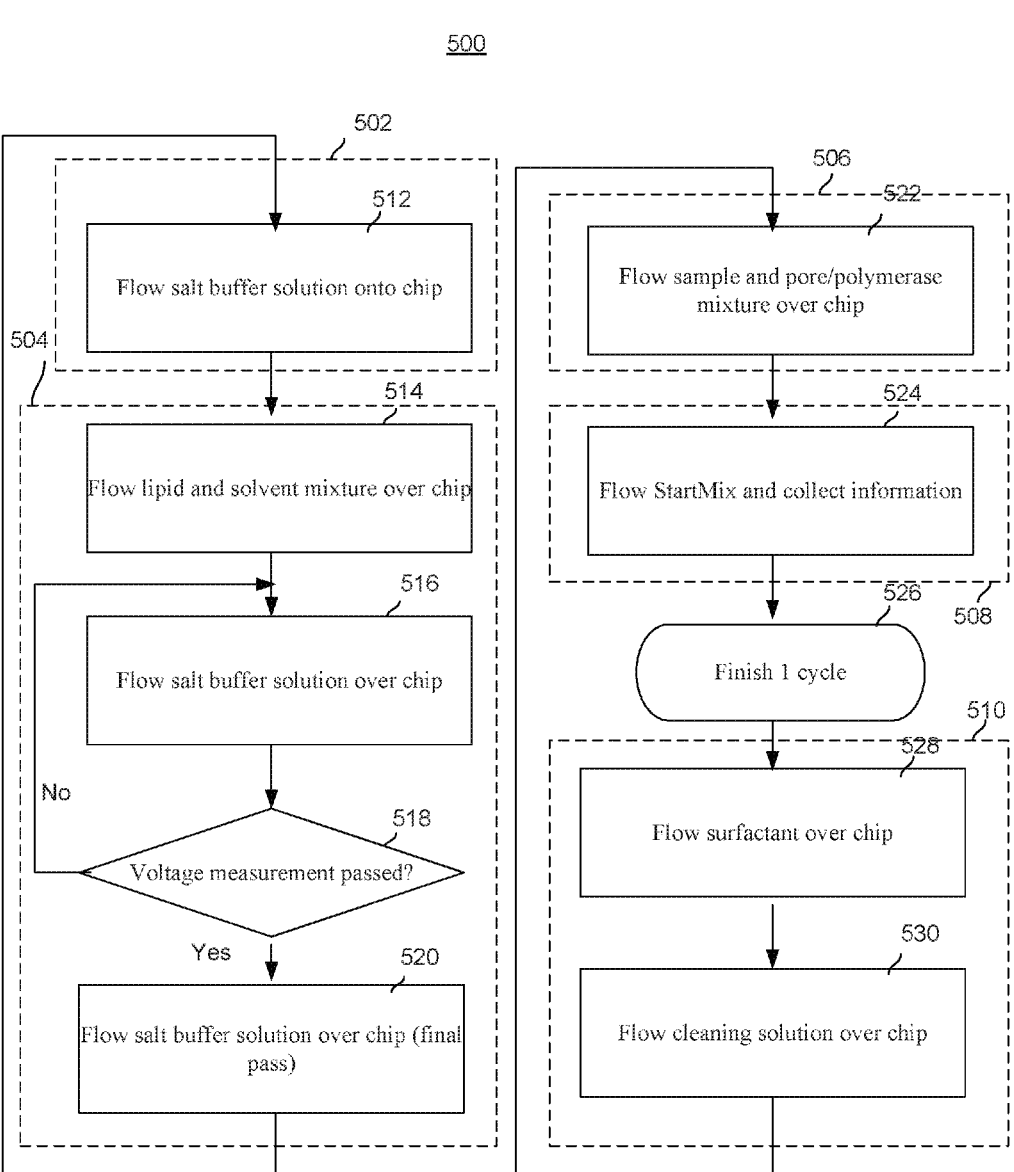
FIG. 5 illustrates an embodiment of a fluidic workflow process 500 for flowing different types of liquids or gases through the cells of a nanopore based sequencing chip during different phases of the chip's operation.

FIG. 5 illustrates an embodiment of a fluidic workflow process 500 for flowing different types of fluids (liquids or gases) through the cells of a nanopore based sequencing chip during different phases of the chip's operation. The nanopore based sequencing chip operates in different phases, including an initialization and calibration phase (phase 502), a membrane formation phase (phase 504), a nanopore formation phase (phase 506), a sequencing phase (phase 508), and a cleaning and reset phase (phase 510).

At the initialization and calibration phase 502, a salt buffer is flowed through the cells of the nanopore based sequencing chip at 512. The salt buffer may be potassium chloride (KCl), potassium acetate (KAc), sodium trifluoroacetate (NaTFA), and the like.

At the membrane formation phase 504, a membrane, such as a lipid bilayer, is formed over each of the cells. At 514, a lipid and decane mixture is flowed over the cells. At 516, a salt buffer is flowed over the cells. At 518, voltage measurements across the lipid bilayers are made to determine whether the lipid bilayers are properly formed. If it is determined that the lipid bilayers are not properly formed, then step 516 is repeated; otherwise, the process proceeds to step 520. At 520, a salt buffer is again introduced.

At the nanopore formation phase 506, a nanopore is formed in the bilayer over each of the cells. At 522, a sample and a pore/polymerase mixture are flowed over the cells.

At the sequencing phase 508, DNA sequencing is performed. At 524, StartMix is flowed over the cells, and the sequencing information is collected and stored. StartMix is a reagent that initiates the sequencing process. After the sequencing phase, one cycle of the process is completed at 526.

At the cleaning and reset phase 510, the nanopore based sequencing chip is cleaned and reset such that the chip can be recycled for additional uses. At 528, a surfactant is flowed over the cells. At 530, ethanol is flowed over the cells. In this example, a surfactant and ethanol are used for cleaning the chip. However, alternative fluids may be used. Steps 528 and 530 may also be repeated a plurality of times to ensure that the chip is properly cleaned. After step 530, the lipid bilayers and pores have been removed and the fluidic workflow process 500 can be repeated at the initialization and calibration phase 502 again.

As shown in process 500 described above, multiple fluids with significantly different properties (e.g., compressibility, hydrophobicity, and viscosity) are flowed over an array of sensors on the surface of the nanopore based sequencing chip. For improved efficiency, each of the sensors in the array should be exposed to the fluids or gases in a consistent manner. For example, each of the different types of fluids should be flowed over the nanopore based sequencing chip such that the fluid or gas may be delivered to the chip, evenly coating and contacting each of the cells' surface, and then delivered out of the chip. As described above, a nanopore based sequencing chip incorporates a large number of sensor cells configured as an array. As the nanopore based sequencing chip is scaled to include more and more cells, achieving an even flow of the different types of fluids or gases across the cells of the chip becomes more challenging.

Figure 6A:
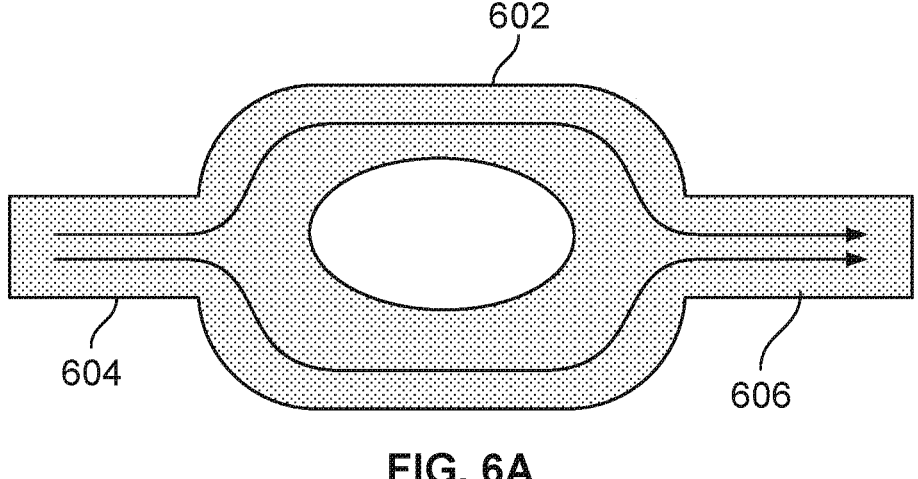
FIG. 6A illustrates an exemplary flow of a liquid or gas across the nanopore based sequencing chip.

FIG. 6A illustrates an exemplary flow of a fluid across the nanopore based sequencing chip. In FIG. 6A, an inlet (e.g., a tube) 604 delivers a fluid to a nanopore based sequencing chip 602, and an outlet 606 delivers the fluid or gas out of the chip. Due to the difference in width between the inlet and the nanopore based sequencing chip, as the fluid or gas enters chip 602, the fluid or gas flows through paths that cover the cells that are close to the outer perimeter but not the cells in the center portion of the chip.

Figure 6B:
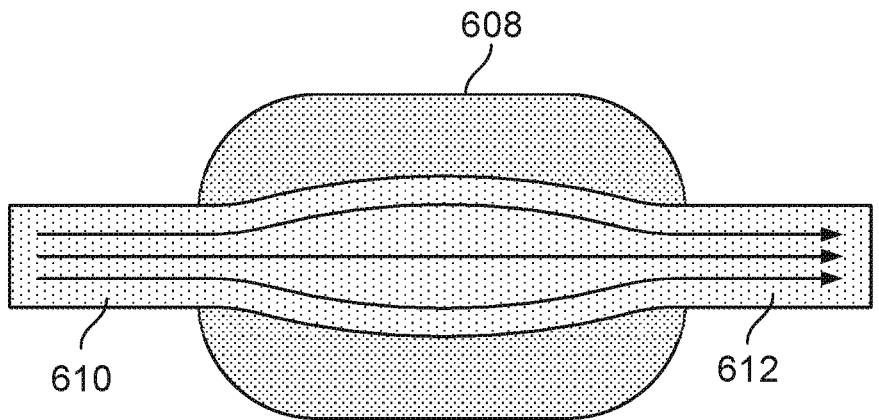
FIG. 6B illustrates another exemplary flow of a liquid or gas across the nanopore based sequencing chip.

FIG. 6B illustrates another exemplary flow of a fluid across the nanopore based sequencing chip. In FIG. 6B, an inlet 610 delivers a fluid to a nanopore based sequencing chip 608, and an outlet 612 delivers the fluid or gas out of the chip. As the fluid or gas enters chip 608, the fluid or gas flows through paths that cover the cells that are close to the center portion of the chip but not the cells that are close to the outer perimeter of the chip.

As shown in FIG. 6A and FIG. 6B above, the nanopore based sequencing chip has one or more "dead" zones in the flow chamber. In the embodiment shown in FIG. 6A, the dead zones are distributed close to the center of the chip. In the embodiment shown in FIG. 6B, the dead zones are distributed close to the outer perimeter of the chip. The sensors in the chip array beneath the dead zones are exposed to a small amount of the fluid or a slow flow of the fluid, while the sensors outside of the dead zones are exposed to an excess or fast flow of the fluid.

Figure 7A:
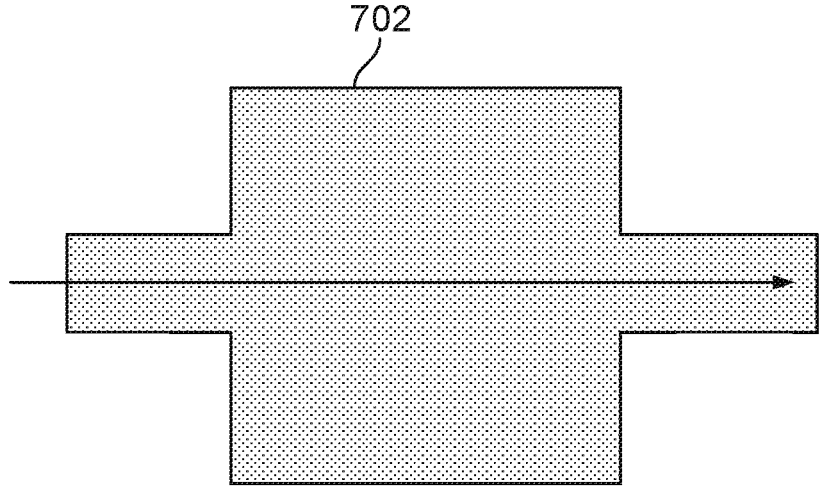
FIG. 7A illustrates an exemplary flow of a first type of fluid across the nanopore based sequencing chip.
Figure 7B:
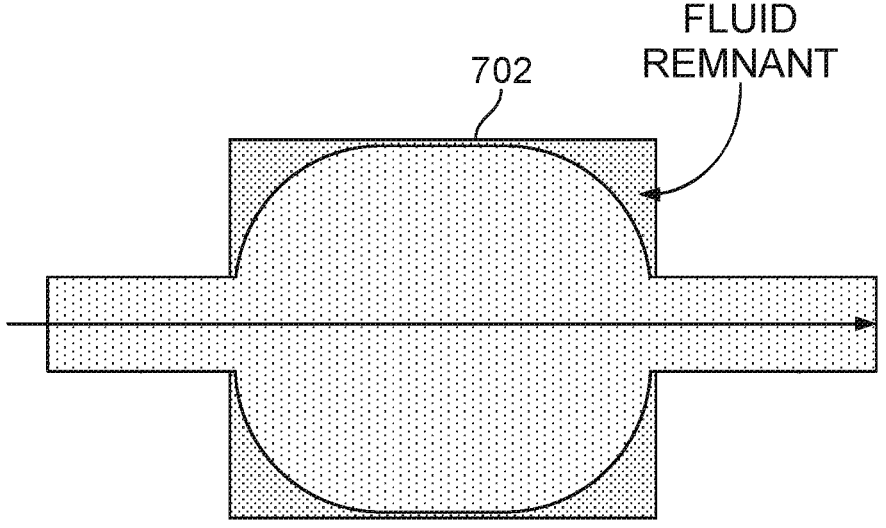
FIG. 7B illustrates that a second fluid is flowed through the chip after a first fluid has been flowed through the chip at an earlier time.

Furthermore, the introduction of a second fluid may not displace the first fluid in the dead zones effectively. FIG. 7A illustrates an exemplary flow of a first type of fluid across the nanopore based sequencing chip. In this example, since the dead zones are located at the corners of the nanopore base sequencing chip, the corners of the chip are exposed to the first fluid later than other portions of the chip, but eventually the corners are finally filled up with the first fluid. FIG. 7B illustrates that a second fluid is flowed through the chip after a first fluid has been flowed through the chip at an earlier time. Because the dead zones are located at the corners of the chip, the second fluid fails to displace the first fluid at the corners within a short period of time. As a result, the sensors in the array are not exposed to the right amount of fluid in a consistent manner.

The design of the flow chamber may also affect the formation of lipid bilayers with the appropriate thickness. With reference to step 514 of process 500 in FIG. 5, a lipid and decane mixture is flowed over the cells, creating a thick lipid layer on top of each of the cells. In order to reduce the thickness of a lipid layer, in some embodiments, one or more air bubbles are flowed over the sensor to scrape the lipid layer into a thinner layer at step 516 of process 500. The design of the flow chamber should be optimized to control the scraping boundary between the air and the lipid layers, such that an even wiping action is performed over all of the sensors. In addition, the design of the flow chamber may be optimized to prevent the air bubbles from collapsing midway across the flow chamber; otherwise, only a portion of the lipid layers in the chip are scraped or "thinned."

With continued reference to FIG. 6 and FIG. 7, when the flow chamber flows the fluid from one end to the opposite end of the chip, the size of the dead zones within the chip and the collapsing of the air bubbles, in some embodiments, may be reduced by controlling the flow of the fluids and the air bubbles using different pressure and velocity. However, the improvement is limited.

Figure 8:
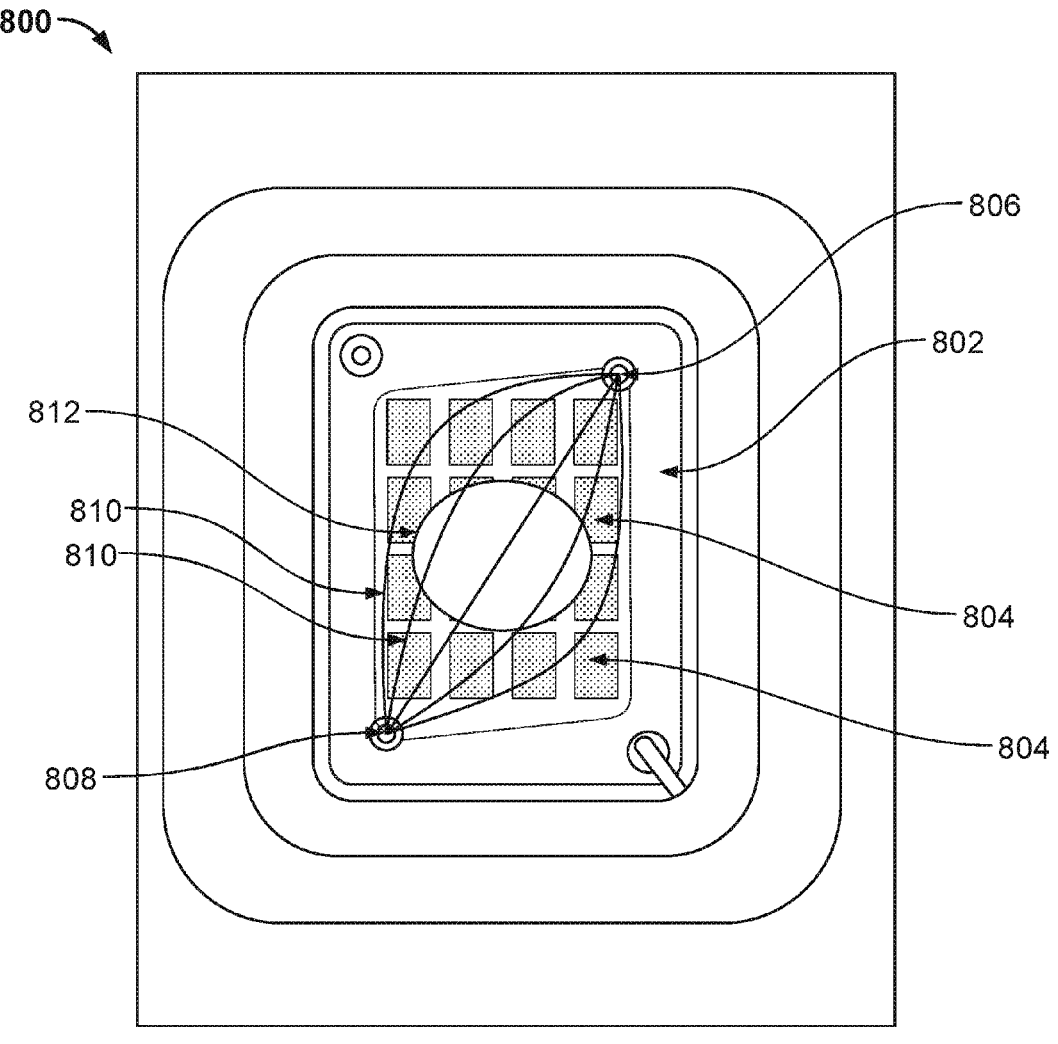
FIG. 8 illustrates the top view of a nanopore based sequencing system 800 with a flow chamber enclosing a silicon chip that allows liquids and gases to pass over and contact sensors on the chip surface.

FIG. 8 illustrates the top view of a nanopore based sequencing system 800 with a flow chamber enclosing a silicon chip that allows liquids and gases to pass over and contact sensors on the chip surface. In this example, the nanopore array chip 802 includes 16 sensor banks (804) in a 4×4 row-column arrangement. However, other arrangements of the sensors cells may be used as well. System 800 includes a counter electrode 812 positioned above the flow chamber. Fluids are directed from an inlet 806 to the flow chamber atop chip 802, and the fluids are directed out of the flow chamber via an outlet 808. The inlet and the outlet may be tubes or needles. Inlet 806 and outlet 808 are each positioned at one of two corners of the nanopore array chip 802 diagonally across from each other. Because the chamber is considerably wider than the inlet's width, as the fluid or gas enters the chamber, the fluid or gas flows through different paths 810 that cover more cells that are close to the center portion of the chip than cells that are close to the remaining two corners of the chip. The fluid or gas travels from one corner to another diagonal corner, leaving trapped fluids in dead zones in the remaining corners.

Figure 9:
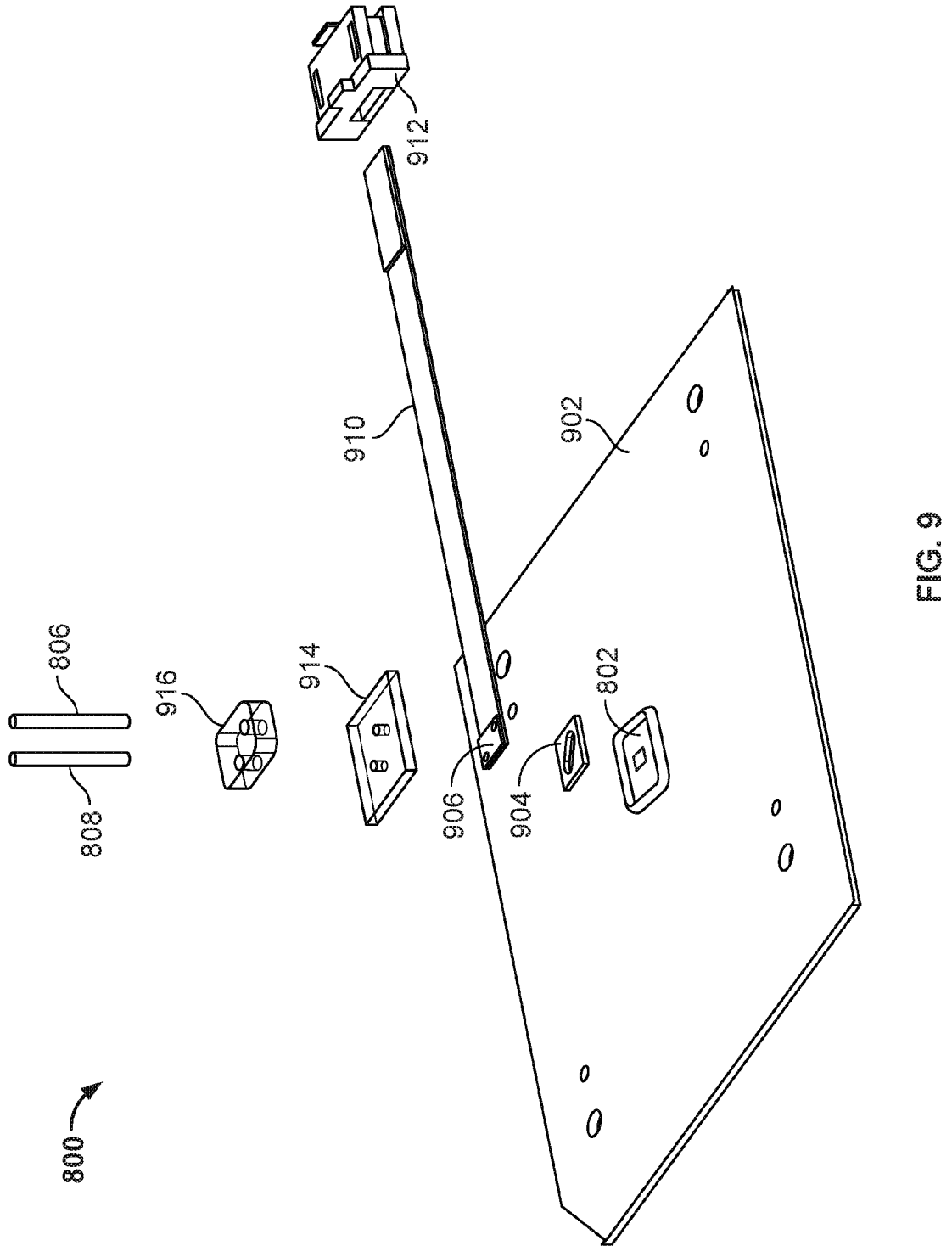
FIG. 9 illustrates the various components that are assembled together to form the nanopore based sequencing system 800 as shown in FIG. 8.

FIG. 9 illustrates the various components that are assembled together to form the nanopore based sequencing system 800 as shown in FIG. 8. System 800 includes various components, including a printed circuit board 902, a nanopore array chip 802, a gasket 904, counter and reference electrodes 906 connected by a flexible flat circuit 910 to a connector 912, a top cover 914, an inlet/outlet guide 916, an inlet 806, and an outlet 808.

Figure 10:
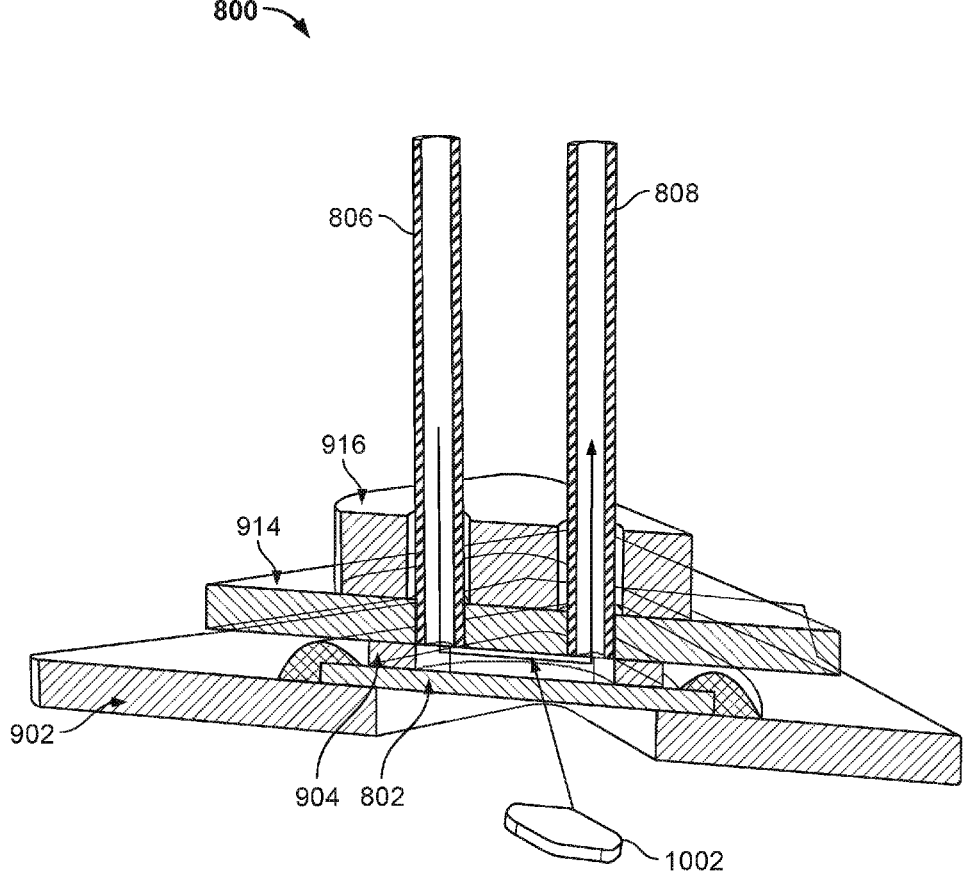
FIG. 10 illustrates another exemplary view of nanopore based sequencing system 800.

FIG. 10 illustrates another exemplary view of nanopore based sequencing system 800. The flow chamber is the space formed between the top cover 914, the gasket 904, and the nanopore array chip 802. The chamber volume is shown as 1002 in FIG. 10.

Figures 11A, 11B:
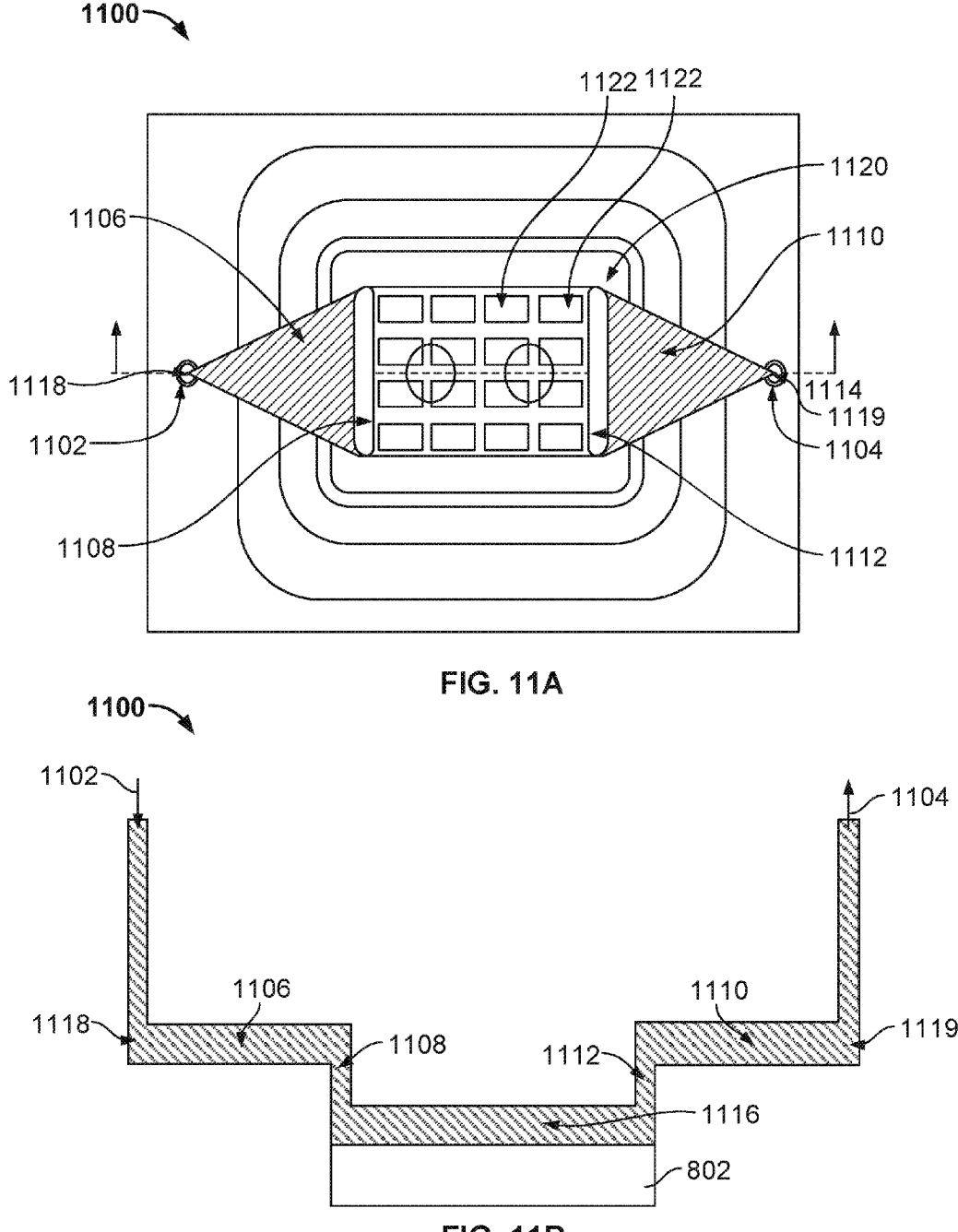
FIG. 11A illustrates the top view of a nanopore based sequencing system 1100 with an improved flow chamber enclosing a silicon chip that allows liquids and gases to pass over and contact sensors on the chip surface.
FIG. 11B illustrates the cross sectional view of system 1100 from the position of a plane 1114 through the system.

FIG. 11A illustrates the top view of a nanopore based sequencing system 1100 with an improved flow chamber enclosing a silicon chip that allows liquids and gases to pass over and contact sensors on the chip surface. FIG. 11B illustrates the cross sectional view of system 1100 from the position of a plane 1114 through the system.

A fluid is directed into system 1100 through an inlet 1102. Inlet 1102 may be a tube or a needle. For example, the tube or needle may have a diameter of one millimeter. Instead of feeding the fluid or gas directly into the flow chamber, inlet 1102 feeds the fluid or gas to a fan-out plenum space or reservoir 1106. As shown in the top view of system 1100 (FIG. 11A), fan-out plenum 1106 directs the fluid or gas outwardly from a central point, a small orifice 1118 of inlet 1102 that intersects (see FIG. 11B) with the fan-out plenum 1106. Fan-out plenum 1106 spreads out from orifice 1118 into a fanlike shape. For example, the fanlike shape as shown in FIG. 11A is a substantially triangular shape. However, other similar shapes that direct the fluid or gas outwardly from the small orifice 1118 may be used as well. In one example, orifice 1118 is one millimeter wide, and fan-out plenum 1106 fans out to seven millimeters, the width of one row of four sensor banks 1122.

With reference to the cross sectional view of system 1100 (FIG. 11B), the fluid or gas fills fan-out plenum 1106 first and then spills over and drains down a narrow slit or slot 1108 that intersects with a flow chamber 1116, like a waterfall. Flow chamber 1116 allows the fluid or gas to pass over and contact sensors on the surface of nanopore array chip 1120. Because slit 1108 spans across a row of sensor banks 1122, the fluid or gas is flowed more evenly across the sensor cells, reducing the number and areas of the dead zones within the chip. As the fluid or gas sweeps across the chip, the fluid or gas reaches a second narrow slit 1112 at the opposite end of the chip, and the fluid or gas is directed through slit 1112 up to a reverse fan-out plenum 1110. Reverse fan-out plenum 1110 directs the fluid or gas towards a central point, a small orifice 1119 of outlet 1104 that intersects (see FIG. 11B) with the reverse fan-out plenum 1110. The fluid or gas is then directed out of system 1100 via an outlet 1104.

Figures 12A, 12B:
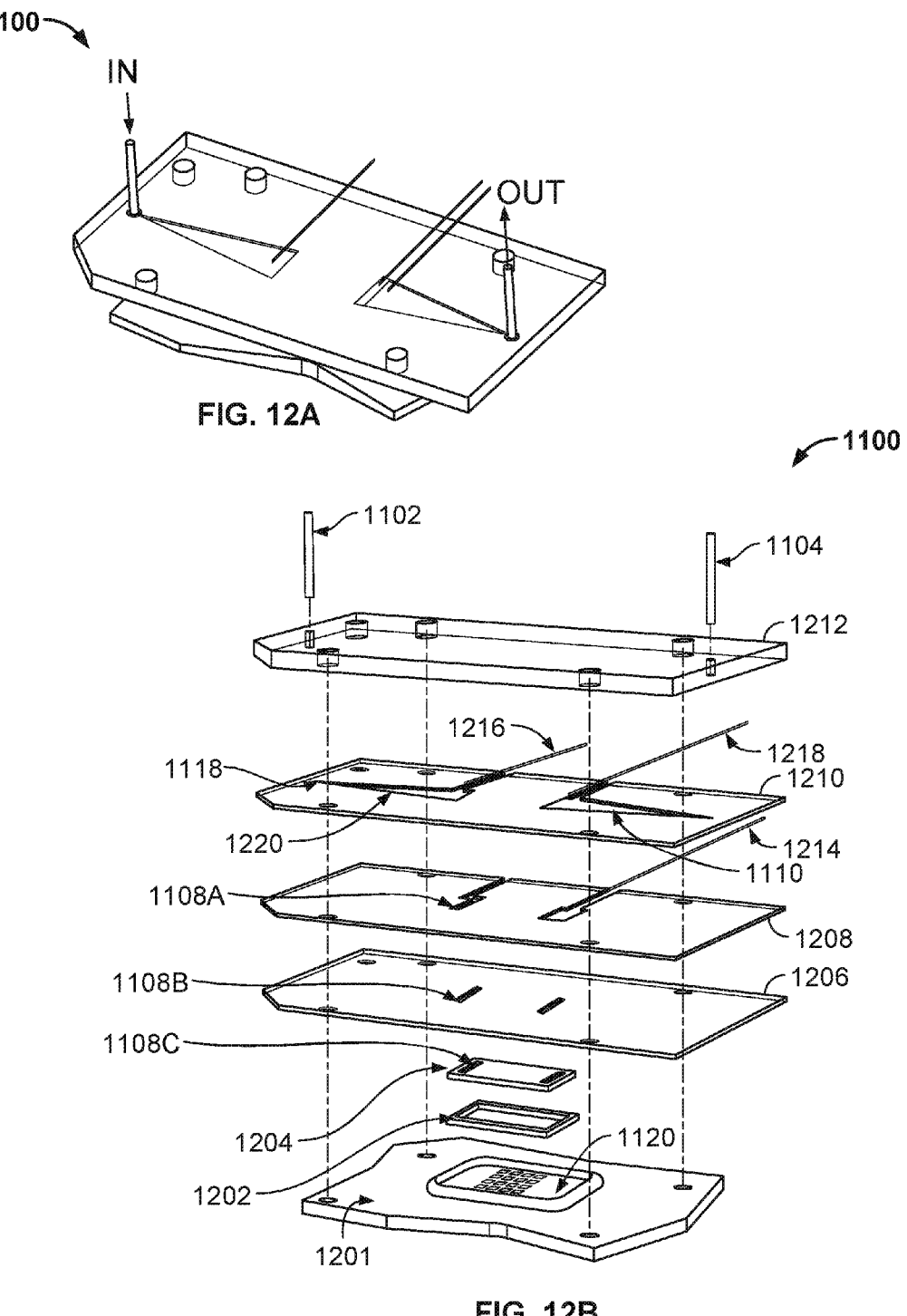
FIG. 12A illustrates another exemplary view of nanopore based sequencing system 1100 with a fan-out plenum.
FIG. 12B illustrates the various components that are assembled together to form nanopore based sequencing system 1100 as shown in FIG. 11.

FIG. 12A illustrates another exemplary view of nanopore based sequencing system 1100 with a fan-out plenum. FIG. 12B illustrates the various components that are assembled together to form nanopore based sequencing system 1100 as shown in FIG. 11. System 1100 includes various components, including a printed circuit board 1201, a nanopore array chip 1120, a gasket 1202, a gasket cover 1204, a middle plate 1206, a middle plate 1208, a reference electrode 1214, a middle plate 1210, a counter electrode 1218, a reference electrode 1216, a top plate 1212, an inlet 1102, and an outlet 1104.

The fan-out plenum is the space formed between top plate 1212, a fan-out void 1220 on the middle layer 1210, and middle layer 1208. Slit 1108 is the space formed by aligning a slit 1108A on middle plate 1208, a slit 1108B on middle plate 1206, and a slit 1108C on gasket cover 1204, and stacking middle plate 1208, middle plate 1206, and gasket cover 1204 on top of each other. The flow chamber is the space formed between gasket cover 1204, gasket 1202, and the nanopore array chip 1120.

Figure 13:
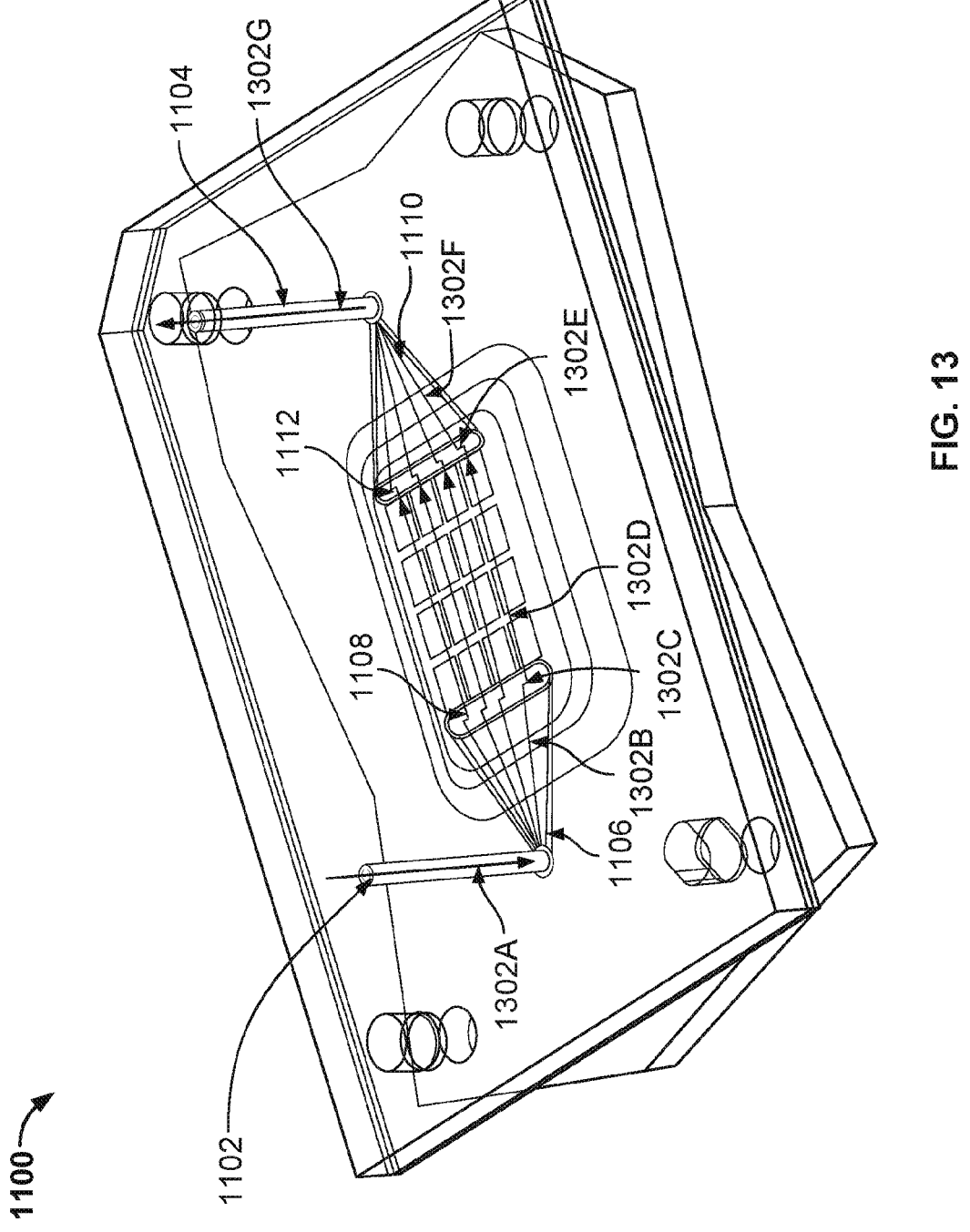
FIG. 13 illustrates the paths that are followed by a fluid as it flows through the nanopore based sequencing system 1100 with a fan-out plenum.

FIG. 13 illustrates the paths that are followed by a fluid as it flows through the nanopore based sequencing system 1100 with a fan-out plenum. A fluid flows down inlet 1102 (see path 1302A), fills fan-out plenum 1106 first (see path 1302B) and then spills over and drains down slit 1108 (see path 1302C) that intersects with the flow chamber. The flow chamber allows the fluid or gas to pass over and contact sensors on the surface of the nanopore array chip as shown in path 1302D. Because slit 1108 spans across a row of sensor banks, the fluid or gas is flowed more evenly across the sensor cells, reducing the number and areas of the dead zones within the chip. As the fluid or gas sweeps across the chip, the fluid or gas reaches slit 1112 at the opposite end of the chip, and the fluid or gas is directed up through slit 1112 (see path 1302E) to a reverse fan-out plenum 1110. Reverse fan-out plenum 1110 converges the fluid or gas towards a central point (see path 1302F), a small orifice of outlet 1104 that intersects with reverse fan-out plenum 1110. The fluid or gas is then directed out of system 1100 via an outlet 1104 as shown in path 1302G.

Figure 14:
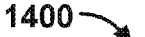
FIG. 14 illustrates the top view of a nanopore based sequencing system 1400 with another improved flow cham-ber enclosing a silicon chip that allows liquids and gases to pass over and contact sensors on the chip surface.
Figure 14:
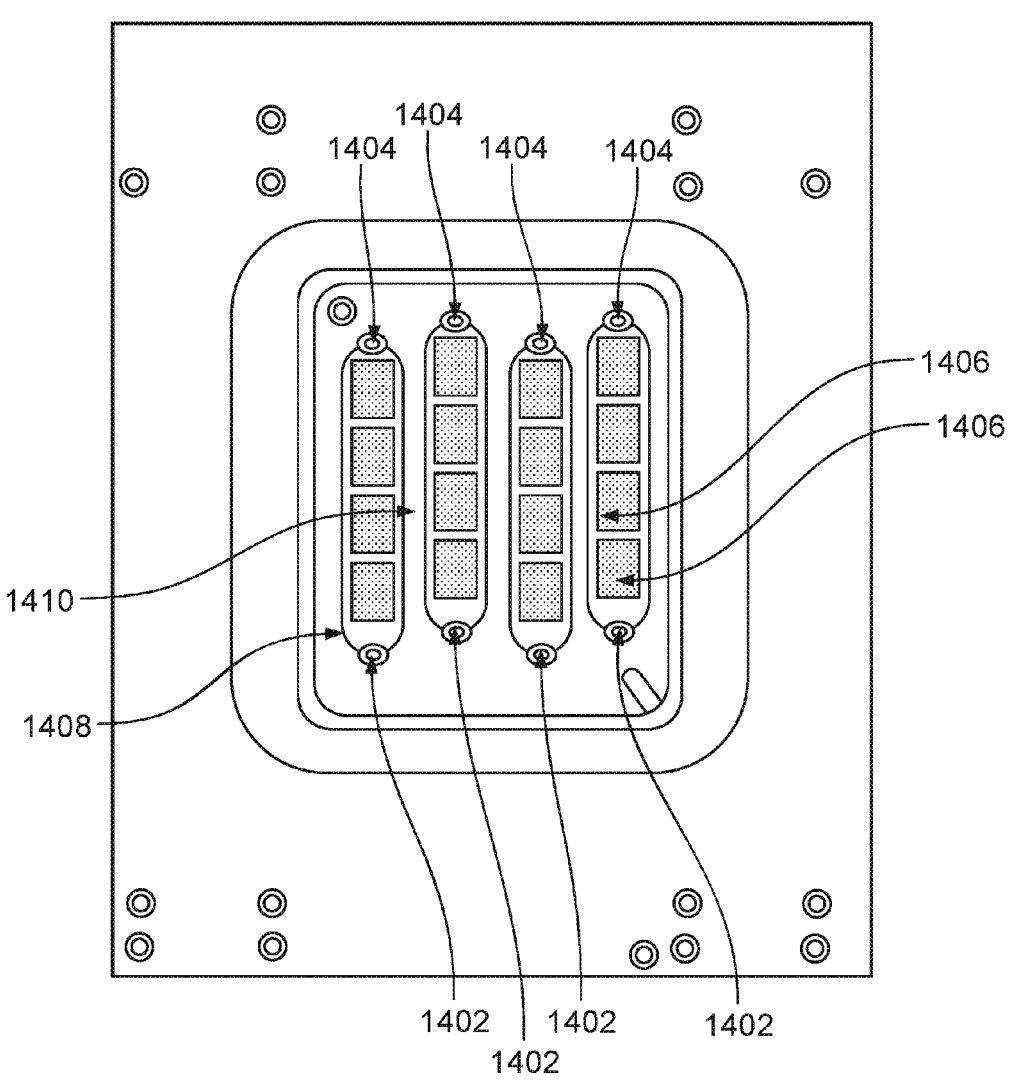

FIG. 14 illustrates the top view of a nanopore based sequencing system 1400 with another improved flow chamber enclosing a silicon chip that allows liquids and gases to pass over and contact sensors on the chip surface. The flow chamber is divided into multiple channels 1408, each channel 1408 directing the fluids to flow directly above a single column (or a single row) of sensor banks 1406. As shown in FIG. 14, system 1400 includes four inlets 1402 and four outlets 1404.

With reference to FIG. 14, a fluid is directed into system 1400 in parallel through the four inlets 1402. Inlet 1402 may be a tube or a needle. For example, the tube or needle may have a diameter of one millimeter. Instead of feeding the fluid or gas directly into a wide flow chamber with a single continuous space, each of the inlets 1402 feeds the fluid or gas into a separate channel 1408 that directs the fluid or gas to flow directly above a single column of sensor banks 1406. The channels 1408 may be formed by stacking together a top plate and a gasket with dividers 1410 that divide the chamber into channels, and then mounting them on top of the chip. Once the fluid or gas flows through the channels 1408 to the opposite side of the chip, the fluid or gas is directed up in parallel through the four outlets 1404 and out of system 1400.

Figure 15:
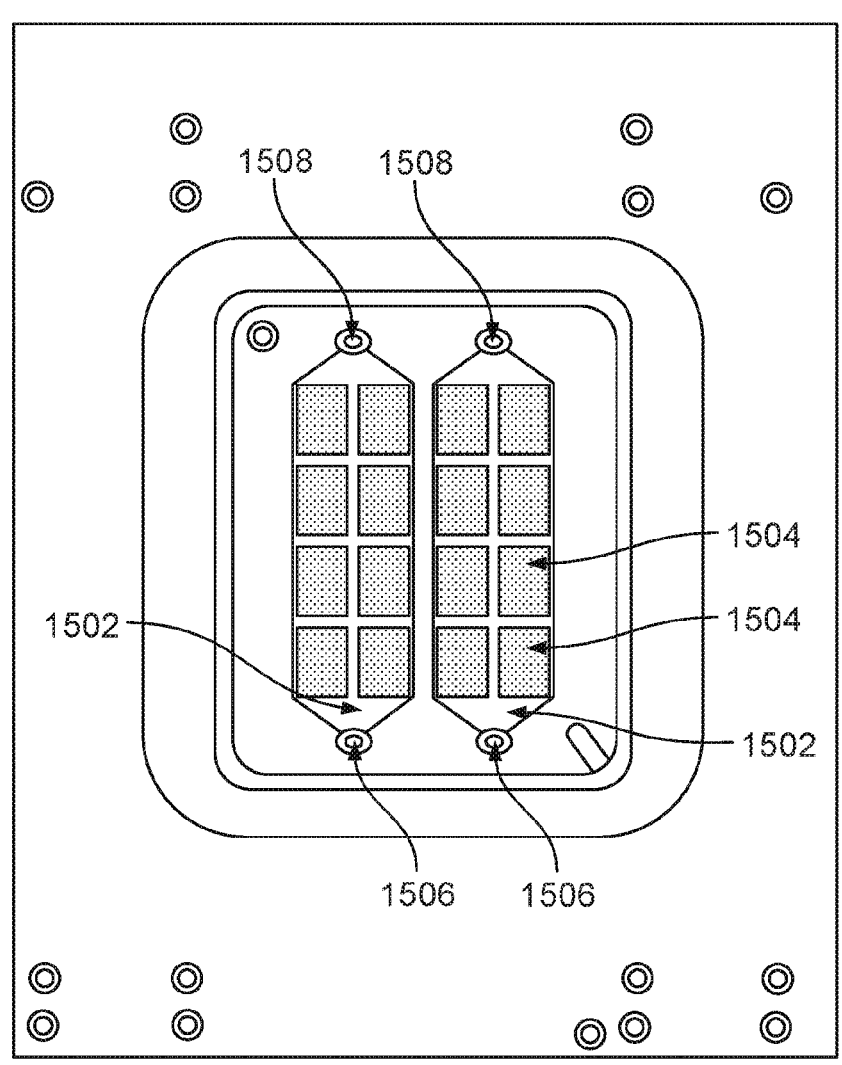
FIG. 15 illustrates the top view of a nanopore based sequencing system 1500 with another improved flow cham-ber enclosing a silicon chip that allows liquids and gases to pass over and contact sensors on the chip surface.

FIG. 15 illustrates the top view of a nanopore based sequencing system 1500 with another improved flow chamber enclosing a silicon chip that allows liquids and gases to pass over and contact sensors on the chip surface. Similar to system 1400, the flow chamber in system 1500 is divided into multiple channels 1502, but each channel 1502 directs the fluids to flow directly above two columns (or two rows) of sensor banks 1504. The width of the channels is about 3.5 millimeters. As shown in FIG. 15, system 1500 includes two inlets 1506 and two outlets 1508.

Both system 1400 and system 1500 allow the fluids to flow more evenly on top of all the sensors on the chip surface. The channel width is configured to be narrow enough such that capillary action has an effect. More particularly, the surface tension (which is caused by cohesion within the fluid) and adhesive forces between the fluid and the enclosing surfaces act to hold the fluid together, thereby preventing the fluid or the air bubbles from breaking up and creating dead zones. Therefore, when the width of a sensor bank is narrow enough, each of the flow channels may flow the fluids directly above two or more columns (or two or more rows) of sensor banks. In this case, system 1500 may be used. When the width of a sensor bank is not narrow enough, then each of the flow channels may flow the fluids directly above one column (or one row) of sensor banks only. In this case, system 1400 may be used.

Figure 16:
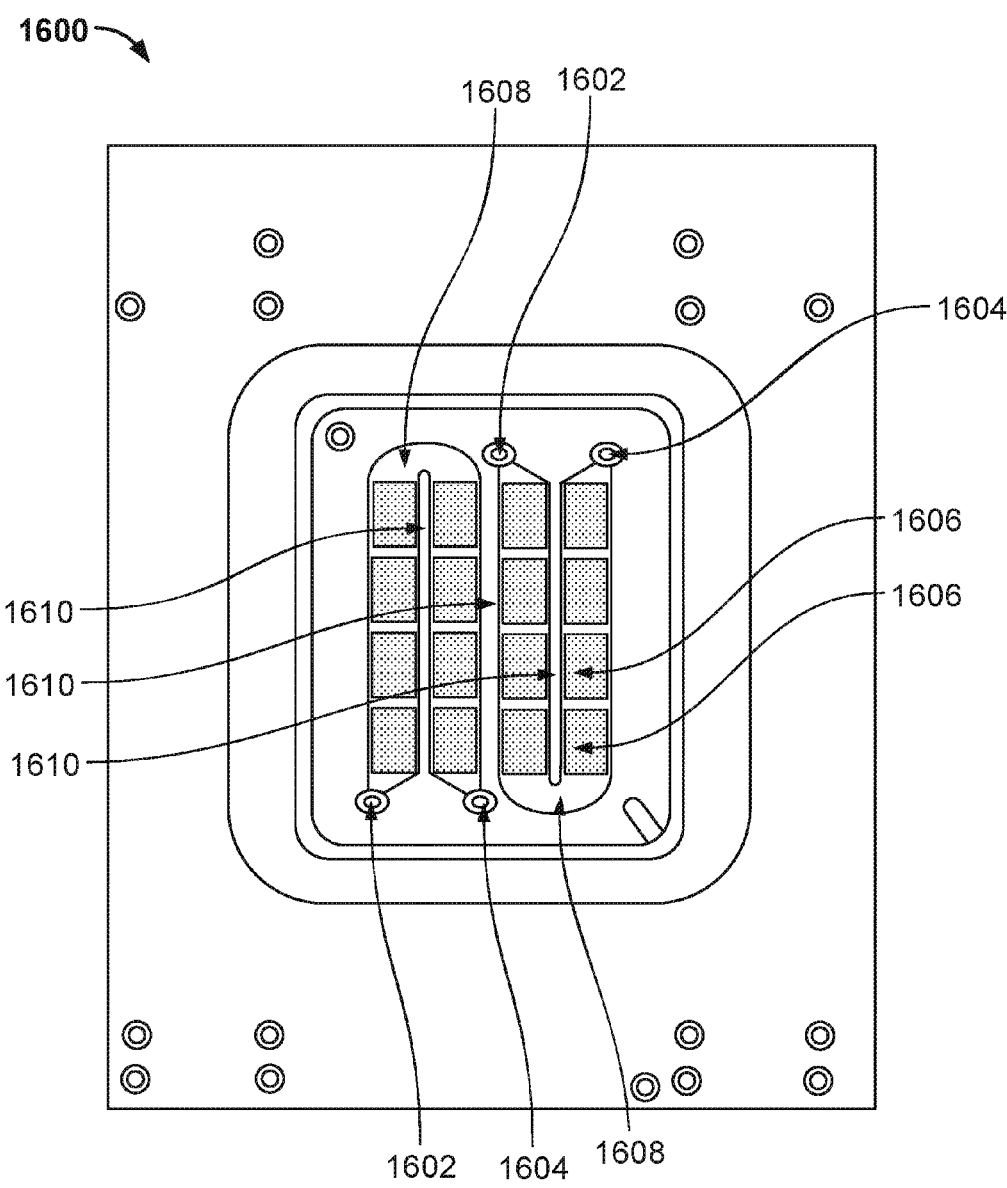
FIG. 16 illustrates the top view of a nanopore based sequencing system 1600 with another improved flow cham-ber enclosing a silicon chip that allows liquids and gases to pass over and contact sensors on the chip surface.

FIG. 16 illustrates the top view of a nanopore based sequencing system 1600 with another improved flow chamber enclosing a silicon chip that allows liquids and gases to pass over and contact sensors on the chip surface. The flow chamber is divided into two horseshoe-shaped flow channels 1608, each channel 1608 directing the fluids to flow directly above a single column (or a single row) of sensor banks 1606 from one end of the chip to the opposite end and then directing the fluids to loop back and flow directly above a second adjacent column of sensor banks to the original end of the chip. As shown in FIG. 16, system 1600 includes two inlets 1602 and two outlets 1604.

With reference to FIG. 16, a fluid is directed into system 1600 in parallel through the two inlets 1602. Inlet 1602 may be a tube or a needle. For example, the tube or needle may have a diameter of one millimeter. Instead of feeding the fluid or gas directly into a wide flow chamber with a single continuous space, each of the inlets 1602 feeds the fluid or gas into a separate channel 1608 that directs the fluid or gas to flow directly above a single column of sensor banks 1606. The channels 1608 may be formed by stacking together a top plate and a gasket with dividers 1610 that divide the chamber into channels, and then mounting them on top of the chip. Once the fluid or gas flows through the channels 1608, the fluid or gas is directed up in parallel through the two outlets 1604 and out of system 1600.

Figure 17:
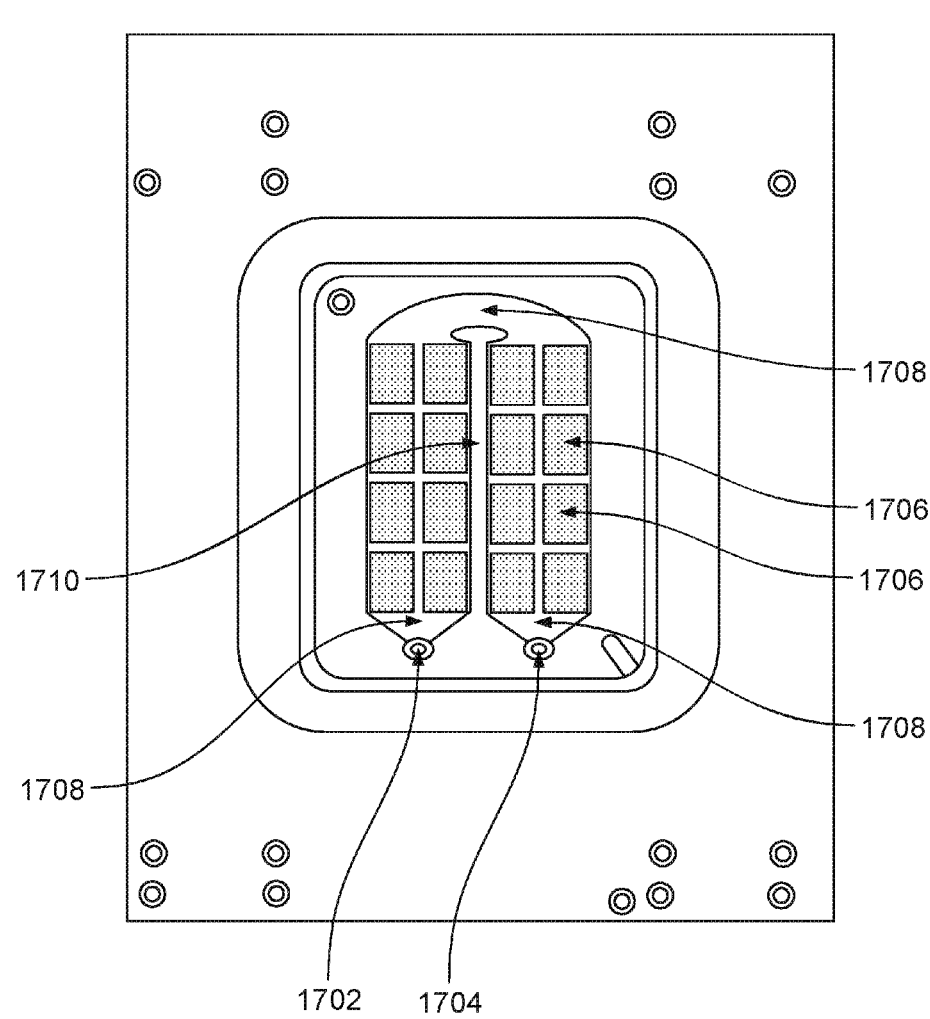
FIG. 17 illustrates the top view of a nanopore based sequencing system 1700 with another improved flow cham-ber enclosing a silicon chip that allows liquids and gases to pass over and contact sensors on the chip surface.

FIG. 17 illustrates the top view of a nanopore based sequencing system 1700 with another improved flow chamber enclosing a silicon chip that allows liquids and gases to pass over and contact sensors on the chip surface. Similar to system 1600, the flow chamber in system 1700 includes a horseshoe-shaped flow channel 1708, but horseshoe-shaped flow channel 1708 directs the fluids to flow directly above two columns (or two rows) of sensor banks 1706. The width of the channel is about 3.5 millimeters. As shown in FIG. 17, system 1700 includes an inlet 1702 and an outlet 1704.

Both system 1700 and system 1700 allow the fluids to flow more evenly on top of all the sensors on the chip surface. The channel width is configured to be narrow enough such that capillary action has an effect. More particularly, the surface tension (which is caused by cohesion within the fluid) and adhesive forces between the fluid and the enclosing surfaces act to hold the fluid together, thereby preventing the fluid or the air bubbles from breaking up and creating dead zones. Therefore, when the width of a sensor bank is narrow enough, each of the horseshoe-shaped flow channels may flow the fluids directly above two or more columns (or two or more rows) of sensor banks. In this case, system 1700 may be used. When the width of a sensor bank is not narrow enough, then each of horseshoe-shaped flow channels may flow the fluids directly above one column (or one row) of sensor banks only. In this case, system 1600 may be used.

Figure 18:
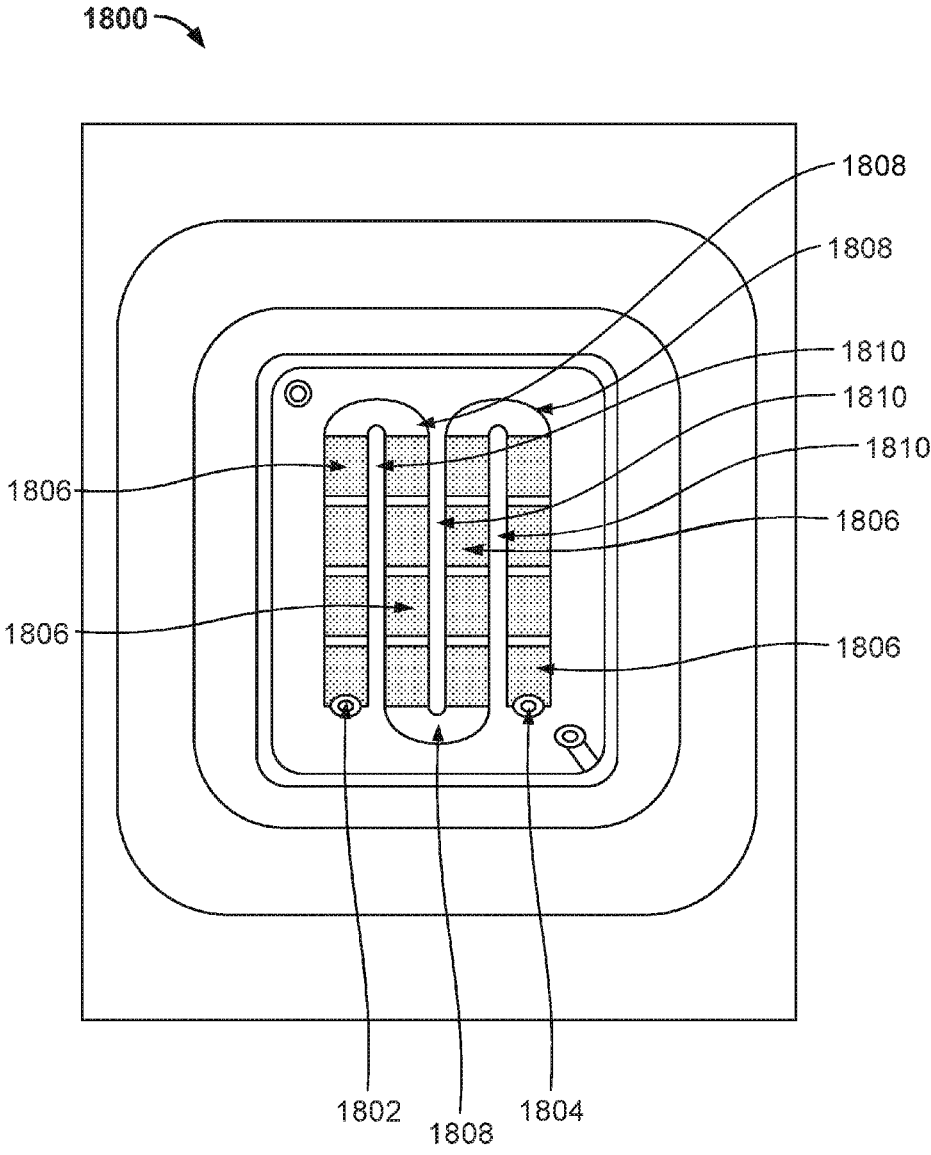
FIG. 18 illustrates the top view of a nanopore based sequencing system 1800 with another improved flow cham-ber enclosing a silicon chip that allows liquids and gases to pass over and contact sensors on the chip surface.

In some embodiments, the nanopore based sequencing system includes an improved flow chamber having a serpentine fluid flow channel that directs the fluids to traverse over different sensors of the chip along the length of the channel. FIG. 18 illustrates the top view of a nanopore based sequencing system 1800 with an improved flow chamber enclosing a silicon chip that allows liquids and gases to pass over and contact sensors on the chip surface. The flow chamber includes a serpentine or winding flow channel 1808 that directs the fluids to flow directly above a single column (or a single row) of sensor banks 1806 from one end of the chip to the opposite end and then directs the fluids to repeatedly loop back and flow directly above other adjacent columns of sensor banks until all of the sensor banks have been traversed at least once. As shown in FIG. 18, system 1800 includes an inlet 1802 and an outlet 1804 and the serpentine or winding flow channel 1808 directs a fluid to flow from the inlet 1802 to the outlet 1804 over all 16 sensor banks 1806.

With reference to FIG. 18, a fluid is directed into system 1800 through inlet 1802. Inlet 1802 may be a tube or a needle. For example, the tube or needle may have a diameter of one millimeter. Instead of feeding the fluid or gas directly into a wide flow chamber with a single continuous space, inlet 1802 feeds the fluid or gas into a serpentine flow channel 1808 that directs the fluid or gas to flow directly above the columns of sensor banks 1806 serially connected together through serpentine flow channel 1808. The serpentine channel 1808 may be formed by stacking together a top plate and a gasket with dividers 1810 that divide the chamber into the serpentine channel, and then mounting them on top of the chip. Once the fluid or gas flows through the serpentine channel 1808, the fluid or gas is directed up through outlet 1804 and out of system 1800.

System 1800 allows the fluids to flow more evenly on top of all the sensors on the chip surface. The channel width is configured to be narrow enough such that capillary action has an effect. More particularly, the surface tension (which is caused by cohesion within the fluid) and adhesive forces between the fluid and the enclosing surfaces act to hold the fluid together, thereby preventing the fluid or the air bubbles from breaking up and creating dead zones. For example, the channel may have a width of 1 millimeter or less. The narrow channel enables controlled flow of the fluids and minimizes the amount of remnants from a previous flow of fluids or gases.

Figures 19A, 19B:
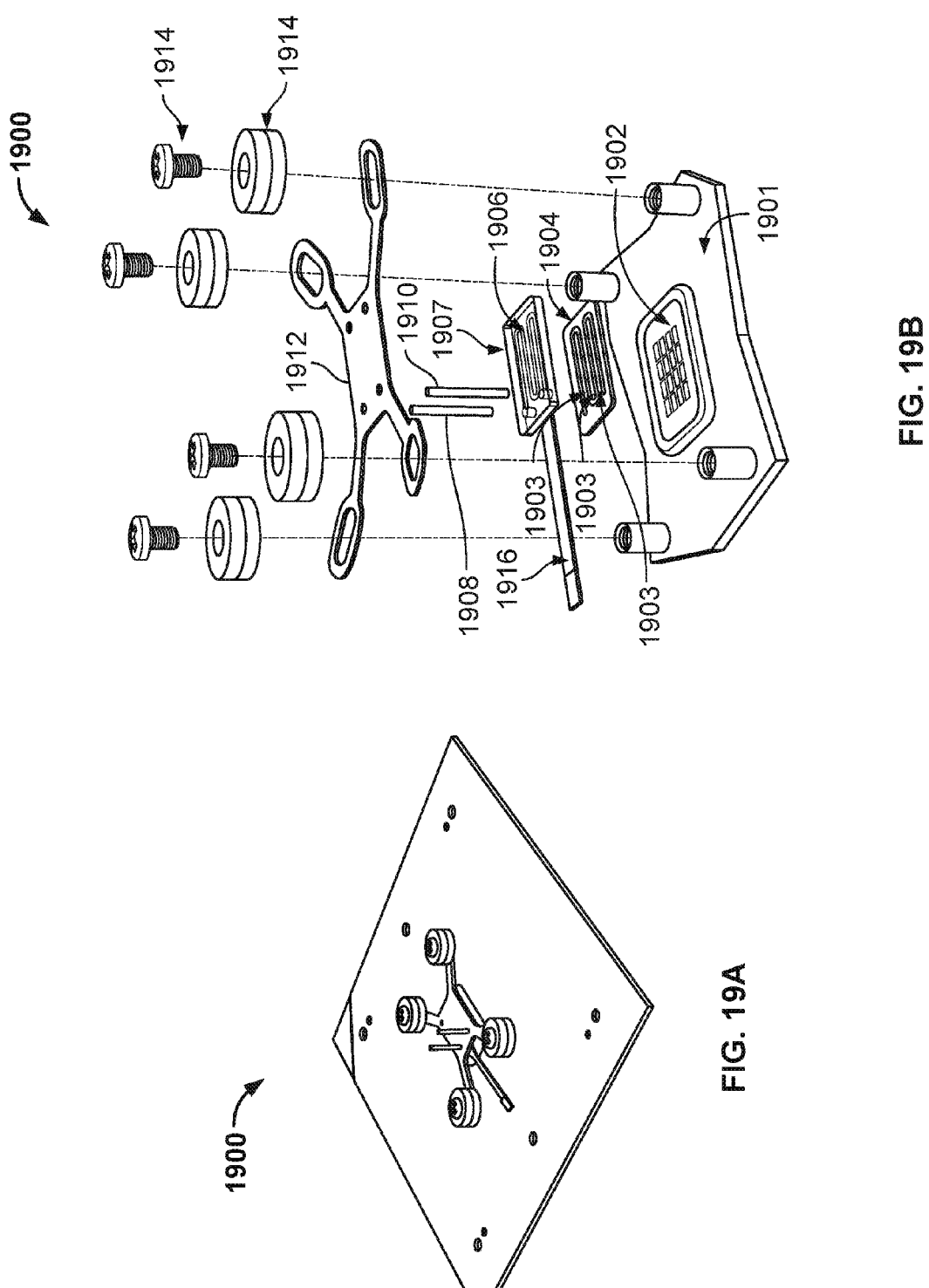
FIG. 19A illustrates an exemplary view of one embodi-ment of a nanopore based sequencing system 1900 with a serpentine flow channel.
FIG. 19B illustrates the various components that are laminated together to form nanopore based sequencing system 1900.

FIG. 19A illustrates an exemplary view of one embodiment of a nanopore based sequencing system 1900 with a serpentine flow channel. FIG. 19B illustrates the various components that are laminated together to form nanopore based sequencing system 1900. System 1900 includes various components, including a printed circuit board 1901, a nanopore array chip 1902, a gasket 1904 with dividers 1903, a backing plate 1907, a counter electrode 1906 on the underside of backing plate 1907, a flexible flat circuit 1916 connecting to counter electrode 1906, an inlet 1908, an outlet 1910, a spring plate 1912, and a plurality of fastening hardware 1914. The serpentine flow channel is the space formed between backing plate 1907, gasket 1904, and nanopore array chip 1902.

Figures 20A, 20B, 20C:
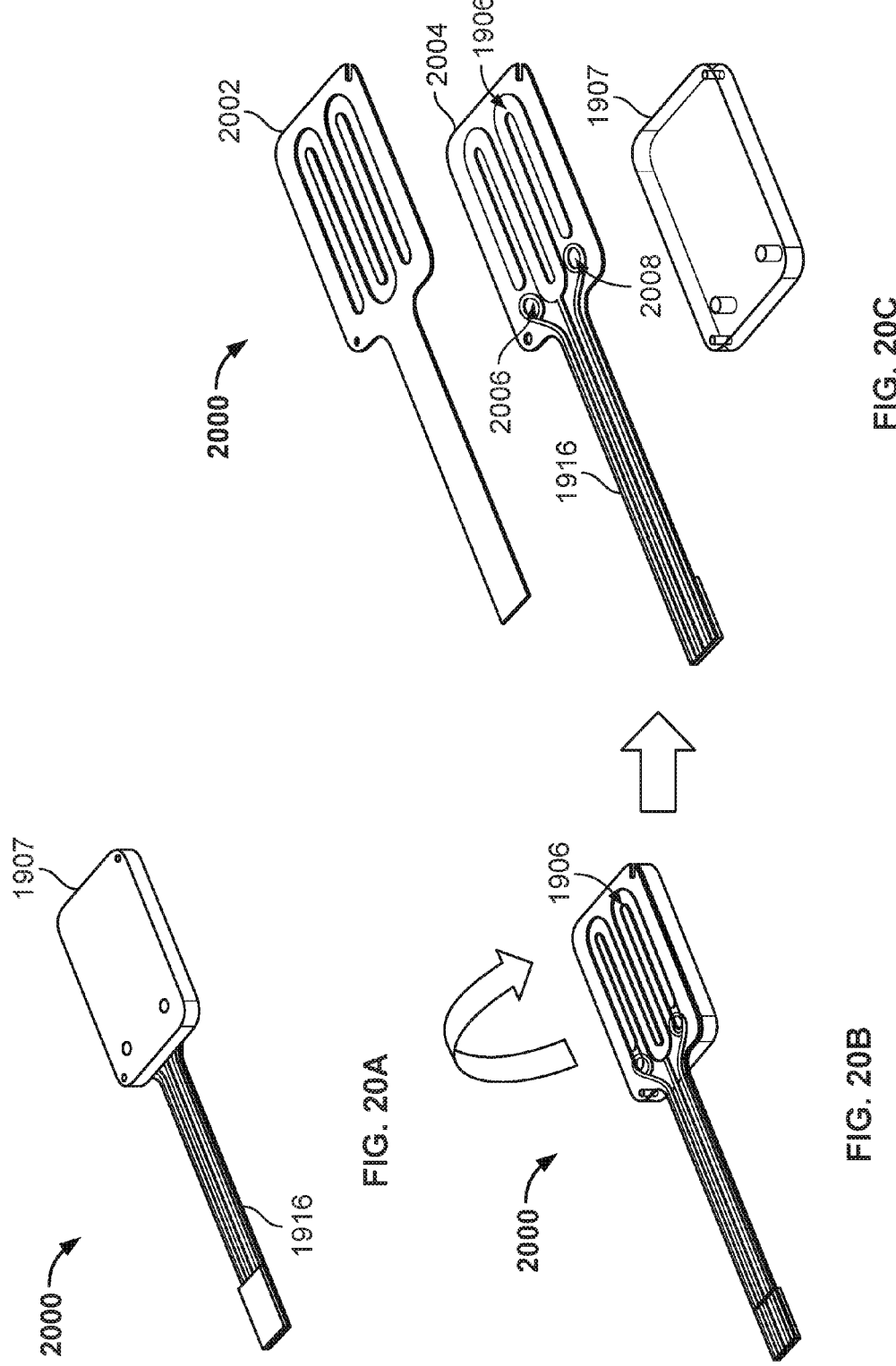
FIG. 20A illustrates the top side view of a backing plate and a flexible flat circuit that is connected to the counter electrode (not visible) located on the bottom side of the backing plate.
FIG. 20B illustrates the same unit 2000 as shown in FIG. 20A when the backing plate is flipped upside down.
FIG. 20C illustrates the various components of unit 2000 that are laminated together.

FIG. 20A illustrates the top side view of a backing plate and a flexible flat circuit that is connected to the counter electrode (not visible) located on the bottom side of the backing plate. FIG. 20B illustrates the same unit 2000 as shown in FIG. 20A when the backing plate is flipped upside down. As shown in this figure, the counter or common electrode 1906 has a serpentine, spiral, or winding shape. Referring back to FIG. 19B, the counter electrode's serpentine shape matches with the serpentine channel of gasket 1904, such that the counter electrode is positioned directly above the sensor banks without being blocked by the dividers 1903 of the gasket. The dividers 1903 are disposed between the sensor banks so that the dividers do not block the flow of the fluids or gases over the sensor banks.

FIG. 20C illustrates the various components of unit 2000 that are laminated together. Unit 2000 includes a dielectric layer 2002, a counter electrode 1906 on a film 2004, a reference electrode 2006, a reference electrode 2008, a flexible flat circuit 1916, and a backing plate 1907.

FIG. 19B and FIG. 20C illustrate that the flow channel is formed by laminating a backing plate with the counter electrode, a gasket, and the silicon chip together. However, the backing plate with the counter electrode and the gasket may be integrated together as a single unit made of the electrode material, and the unit is machined to form the serpentine flow channel.

Figures 21A, 21B, 21C:
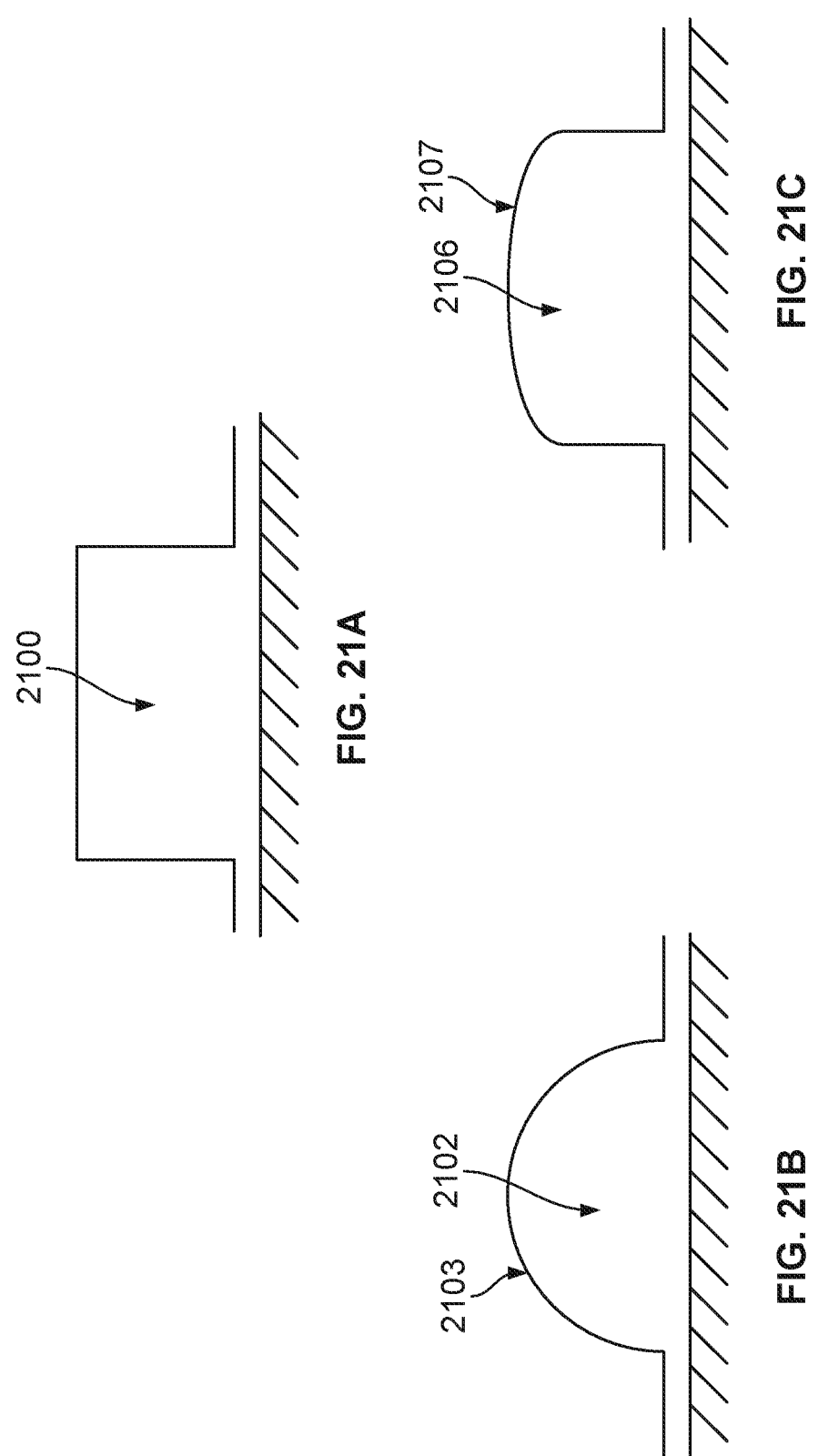
FIG. 21A illustrates a cross sectional view of a flow channel 2100 with sharp edges or sharp corners that may trap fluids more easily.
FIG. 21B illustrates a cross sectional view of a flow channel 2102 that has a D-shaped cross sectional geometry.
FIG. 21C illustrates a cross sectional view of another flow channel 2106 that has a D-shaped cross sectional geometry.
Figure 22:
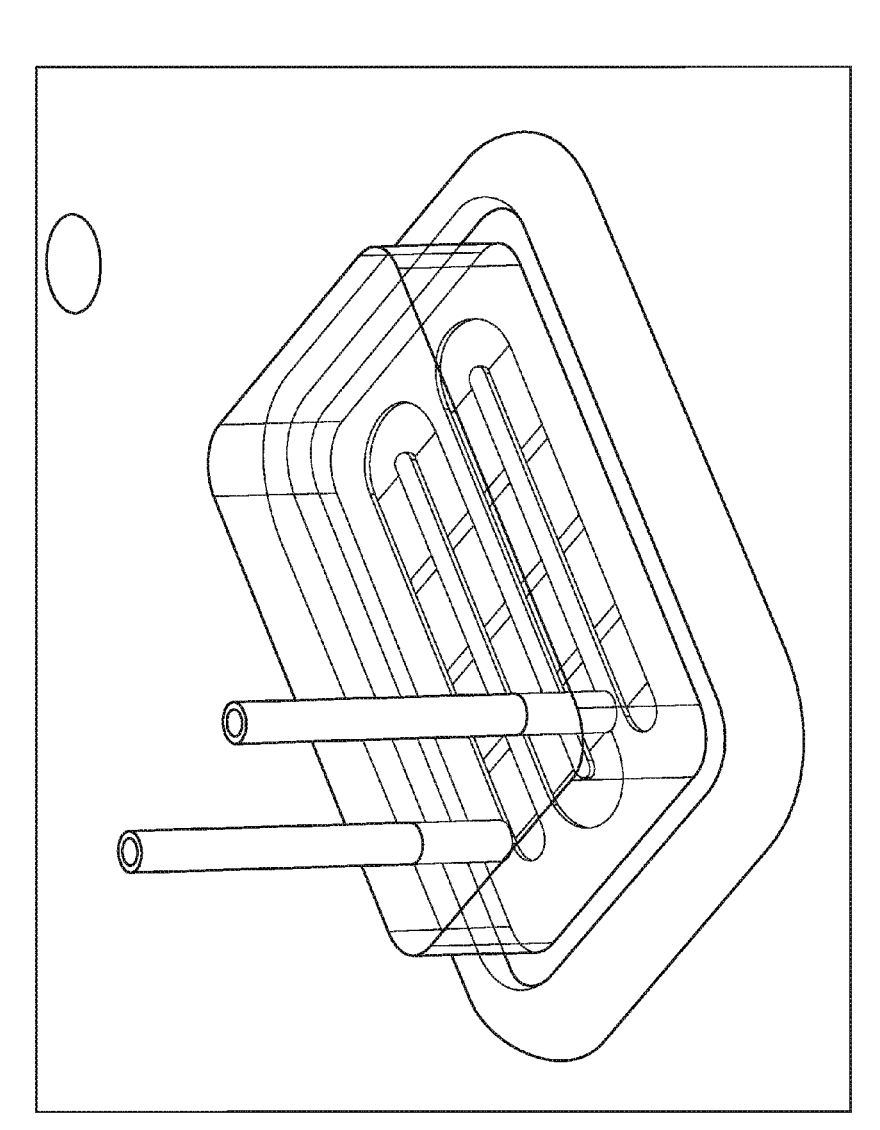
FIG. 22 illustrates a side view of a nanopore based sequencing system with flow channels having a D-shaped cross sectional geometry.

Besides the geometry and dimensions of the flow chamber, other features may also facilitate a more even flow of the fluids on top of all the sensors on the chip surface. FIG. 21A illustrates a cross sectional view of a flow channel 2100 with sharp edges or sharp corners that may trap fluids more easily. FIG. 21B illustrates a cross sectional view of a flow channel 2102 that has a curved roof 2103 and a D-shaped cross-sectional geometry. The sharp edges or sharp corners are replaced by round and smooth surfaces. FIG. 21C illustrates a cross sectional view of another flow channel 2106 that has a curved roof 2107. FIG. 22 illustrates a side view of a nanopore based sequencing system 2200 with flow channels having a D-shaped cross sectional geometry.

Another factor that affects the flow of the fluids on top of all the sensors on the chip surface is the height of the flow channel. For example, the height of the flow channel should be limited to one millimeter or below. In one embodiment, the height of the flow channel is 0.25 millimeters. Other factors that affect the flow of the fluids on top of all the sensors on the chip surface include the surface characteristics of the surfaces defining the flow channel, the flow rate of the fluids, the pressure of the fluid and the gases, and the like.

Figure 23:
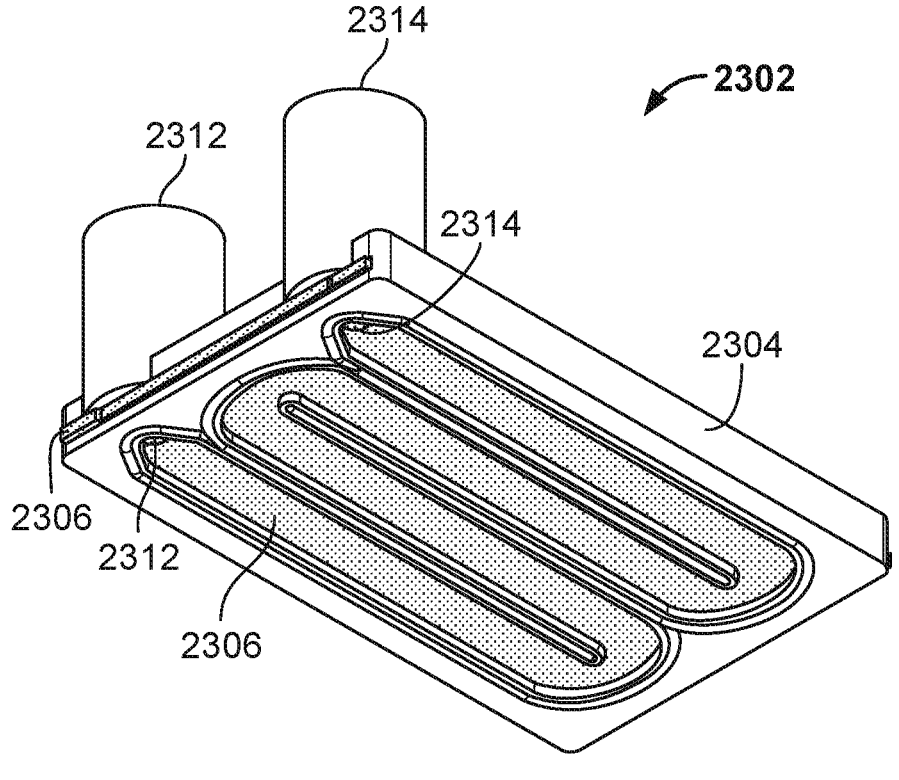
FIG. 23 is a diagram illustrating an embodiment of a molded flow channel component.

FIG. 23 is a diagram illustrating an embodiment of a molded flow channel component. In some embodiments, the component shown in FIG. 23 forms at least a portion of a flow channel shown in FIG. 18. As shown in FIG. 19B, gasket 1904 with dividers 1903 must be carefully aligned with counter electrode 1906 on the underside of backing plate 1907 during assembly to correctly assemble the flow channel. Additionally, as shown in FIG. 20C, dielectric layer 2002, counter electrode 1906, film 2004, and backing plate 1907 must be carefully aligned during assembly. Requiring such a large number of components to be aligned together during assembly introduces complexities that may increase manufacturing cost and risk of error. Therefore, there exists a need for an efficient and reliable way to form the flow channel/chamber of a nanopore system.

Molded flow channel component 2302 includes molded portion 2304 and counter electrode portion 2306. When molded flow channel component 2302 is placed on a nanopore array chip (e.g., chip 1902) and secured, the serpentine void shown in molded flow channel component 2302 (e.g., counter electrode portion 2306 is exposed through the serpentine void of the molded portion 2304) becomes a flow chamber of a fluid flow channel that directs fluids to traverse over different sensors of the nanopore array chip. Molded portion 2304 includes shown raised dividers that guide the fluid flow along the length of the serpentine channel. Molded flow channel component 2302 includes inlet 2312 and outlet 2314. Both inlet 2312 and outlet 2314 include a tubular channel that provides fluid/gas flow in or out of the fluid flow chamber/channel. The inlet/outlet tubular channels are formed at least in part by molded portion 2304 and pass through counter electrode portion 2306.

Molded portion 2304 has been molded over counter electrode portion 2306. For example, counter electrode portion 2306 was placed inside a mold and molding material is injected into the mold to form molded portion 2304 over counter electrode portion 2306 to create molded flow channel component 2302. An example material of molded portion 2304 is an elastomer. An example of counter electrode portion 2306 is a metal (e.g., titanium nitride sputtered/coated stainless steel).

Figure 24:
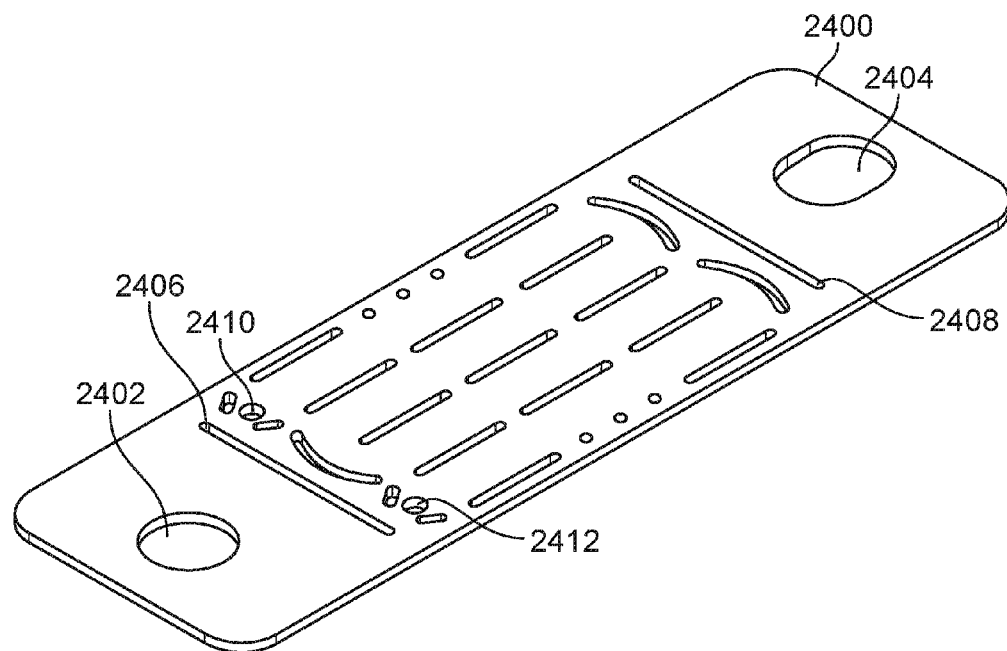
FIG. 24 is a diagram illustrating an embodiment of a counter electrode insert.

FIG. 24 is a diagram illustrating an embodiment of a counter electrode insert. In some embodiments, counter electrode insert 2400 becomes counter electrode portion 2306 of FIG. 23 after assembly. Counter electrode insert 2400 may be made of metal (e.g., stainless steel, steel, aluminum, etc.), semiconductor material (e.g., doped silicon) or other conductive material that may be rigid or flexible (e.g., foil). In some embodiments, counter electrode insert 2400 has been coated and/or sputtered with an electrically conductive material. For example, titanium nitride (TiN) has been sputtered on to a base material (e.g., glass, stainless steel, metal, silicon, etc.) to coat counter electrode insert 2400. This allows the portion of the counter electrode insert 2400 that is exposed inside a flow channel of molded flow channel component 2302 (e.g., portion exposed to chemical reagents) to be titanium nitride. In some embodiments, TiN is a preferred material because of its certain beneficial electrochemical properties, its general availability in and compatibility with existing standard semiconductor manufacturing processes, its compatibility with the biological and chemical reagents, and its relative low cost.

Counter electrode insert 2400 includes cutouts 2402 and 2404 that allow counter electrode insert 2400 to be aligned and stabilized inside an injection mold. Cutouts 2402 and 2404 are on tab ends of counter electrode insert 2400 that are removed (e.g., snapped off) after molding and discarded from counter electrode insert 2400 to form counter electrode portion 2306 of FIG. 23. Cutouts 2406 and 2408 allow the tab ends to be more easily removed (e.g., snapped off) in the direction of the length of the cutouts 2406 and 2408. The tab ends allow easier alignment and stabilization inside a mold as well as easier handling of the component during molding. Cutout 2410 corresponds to inlet 2312 of FIG. 23 and cutout 2412 corresponds to outlet 2314 of FIG. 23 that allows a fluid/gas to pass through counter electrode insert 2400 via tubular channels and in/out of a fluid flow chamber/channel. The other cutouts shown in counter electrode insert 2400 couple counter electrode insert 2400 with a molding material by allowing the molding material to flow through and remain molded in the cutouts to secure the coupling between the counter electrode insert 2400 and the molding material. These other cutouts are placed in locations on the counter electrode insert 2400 to avoid surface portions that are to be exposed inside the fluid chamber/channel. A laser cutter may be utilized as well to produce the shown cutouts. In various embodiments, insert 2400 may have been stamped, chemically etched or cut using a water-jet to produce the shown cutouts.

Figure 25:
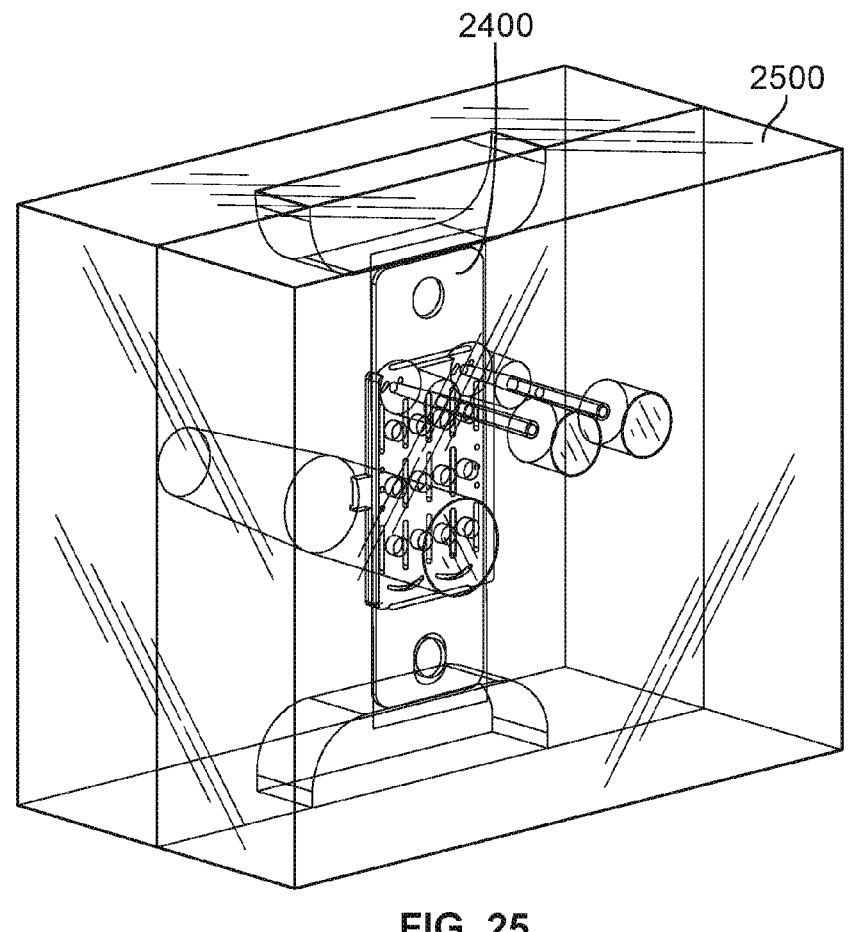
FIG. 25 is a diagram illustrating an embodiment of a mold for a molded flow channel component.

FIG. 25 is a diagram illustrating an embodiment of a mold for a molded flow channel component. In some embodiments, mold 2500 is utilized to produce molded flow channel component 2302 of FIG. 23. A transparent view of mold 2500 is shown to illustrate the internal structure of mold 2500. Mold 2500 includes a plurality of sectional pieces that are joined together when molding a component. These pieces may be separated after molding to extract the molded component. Counter electrode insert 2400 has been placed inside mold 2500. Mold 2500 includes tube features that are inserted in cutouts 2410 and 2412 of counter electrode insert 2400 to produce inlet/outlet tubular channels of molded flow channel component 2302. Counter electrode insert 2400 is secured inside mold 2500 via its tab ends, one or more cutouts and features of mold 2500 contacting a surface of counter electrode insert 2400. A molding material is injected into mold 2500 to injection mold the molding material around counter electrode insert 2400 and in the shape of mold 2500. In various embodiments, molding material may be an elastomer, rubber, silicone, polymer, thermoplastics, plastics, or any other injection moldable material. One or more cutouts/holes on counter electrode insert 2400 may be filled with the molding material to couple the molding material with counter electrode insert 2400. In some embodiments, the molding material injected into mold 2500 becomes molded portion 2304 of FIG. 23. In various other embodiments, other molding techniques such as liquid injection molding (LIM), transfer molding, or compression molding are utilized to produce molded flow channel component 2302 of FIG. 23.

Figure 26:
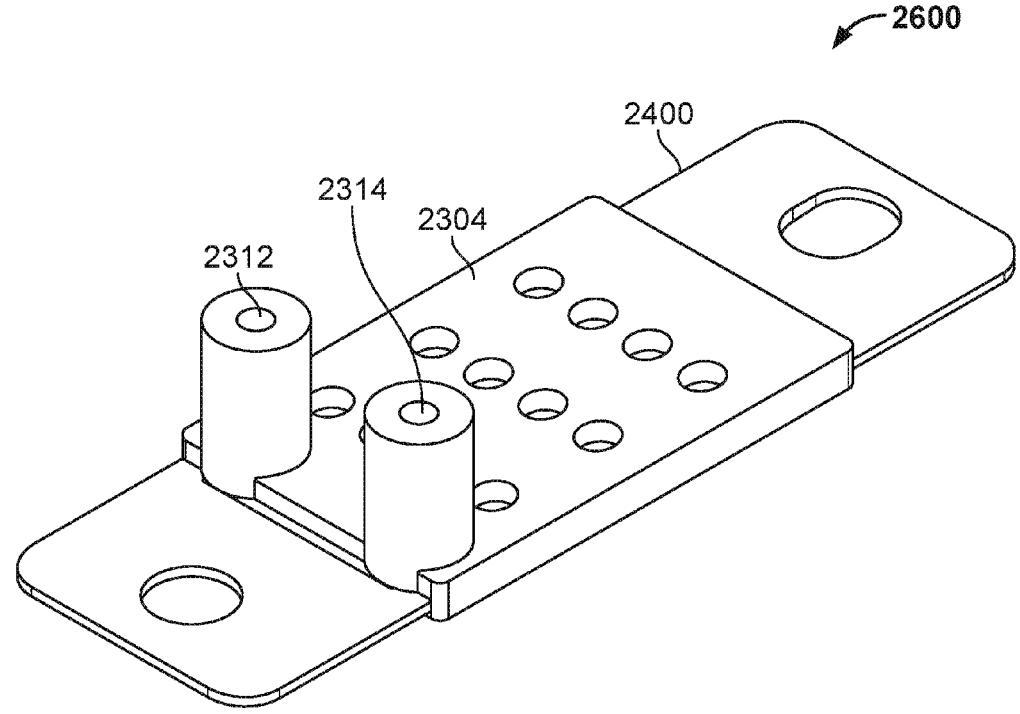
FIG. 26 is a diagram illustrating an embodiment of a molded flow channel component removed from a mold.

FIG. 26 is a diagram illustrating an embodiment of a molded flow channel component removed from a mold. Component 2600 has been removed from mold 2500 after injection molding. After removing (e.g., bending/snapping off) shown end tabs of counter electrode insert 2400, component 2600 becomes molded flow channel component 2302 of FIG. 23. The four by three array of openings/holes on top of molded portion 2304 exposes surfaces of counter electrode insert 2400. In some embodiments, this array of openings/holes is an artifact resulting from the twelve features/pins of mold 2500 that are used to hold and stabilize counter electrode insert 2400 in place in the mold during molding. In some embodiments, at least some of these openings/holes of the array are utilized to make electrical contact with a counter electrode portion. For example, a spring contact is placed in some of the openings/holes of the array and connected to an electrical potential source of a circuit board (e.g., shown in FIG. 27).

Figure 27:
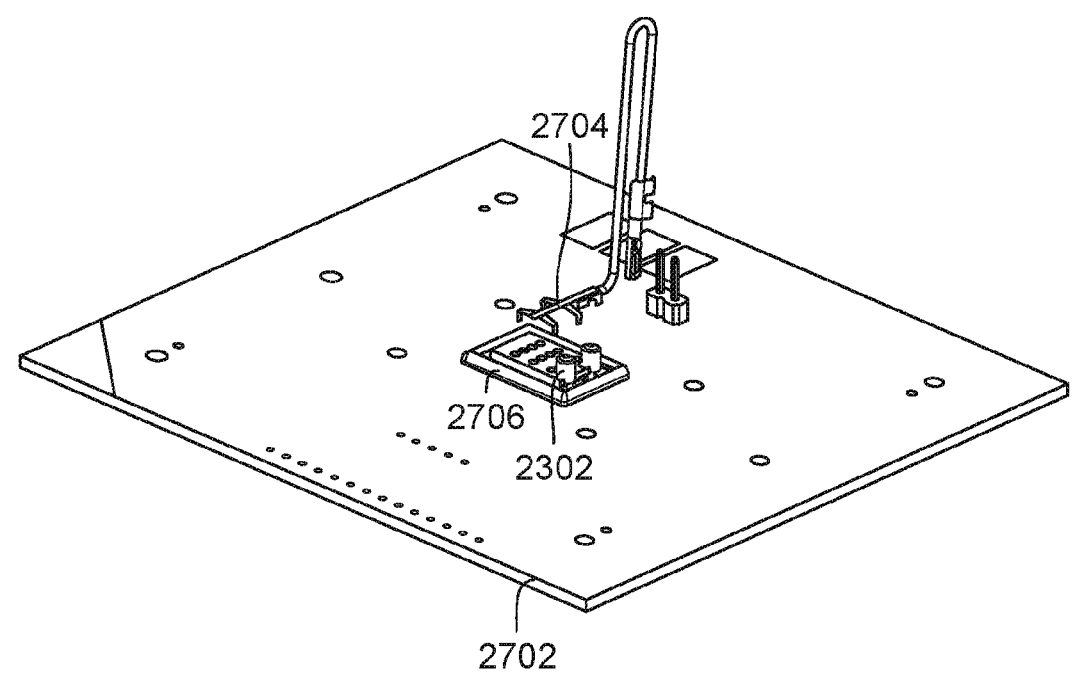
FIG. 27 is a diagram illustrating a portion of an embodiment of a nanopore based sequencing system utilizing a molded flow channel component.

FIG. 27 is a diagram illustrating a portion of an embodiment of a nanopore based sequencing system utilizing a molded flow channel component. Molded flow channel component 2302 has been placed on top of a nanopore array chip that is mounted on circuit board 2702. Spring contact wire component 2704 is to be placed in the array of openings/holes on top of molded flow channel component 2302 to make electrical and physical contact with its counter electrode portion. The other end of spring contact wire component 2704 is to be connected to circuit board 2702 to provide an electrical potential source for its counter electrode. In some embodiments, the molded flow channel component 2302 and electrical contact of spring contact wire component 2704 of the counter electrode are secured and clamped via a clamp plate (e.g., without use of adhesives) that clamps spring contact wire component 2704 to molded flow channel component 2302. In some embodiments, the clamp plate also clamps molded flow channel component 2302 to the nanopore array chip to provide the compression required to seal and couple them together in creating a flow channel/chamber between molded flow channel component 2302 and the nanopore array chip. Encapsulate berm 2706 encapsulates wire bonds between electrical terminals of the nanopore array chip and circuit board 2702.

Figure 28:
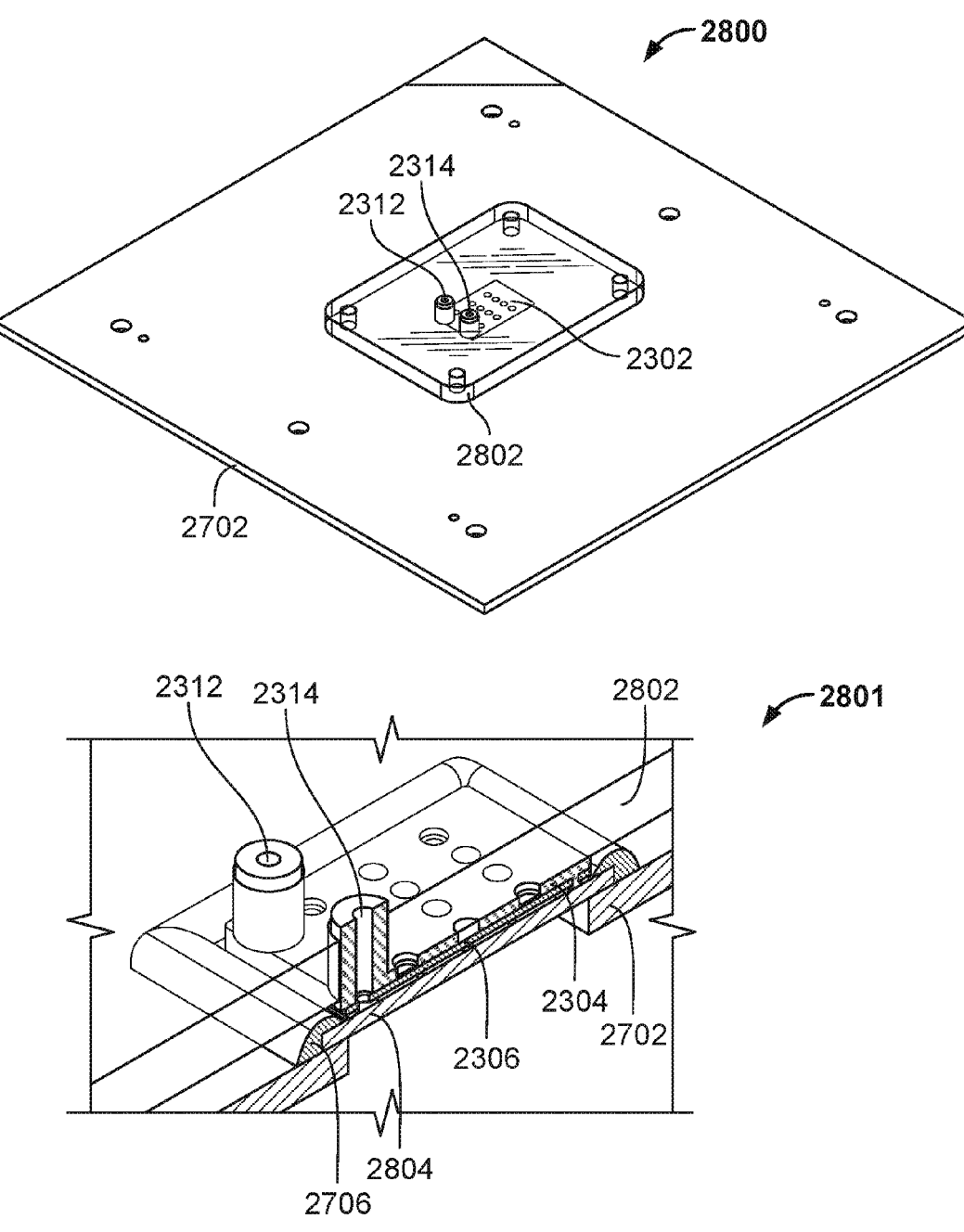
FIG. 28 is a diagram illustrating an embodiment of a clamping of nanopore based sequencing system components.

FIG. 28 is a diagram illustrating an embodiment of a clamping of nanopore based sequencing system components. The views shown in FIG. 28 have been simplified to illustrate the embodiment clearly. View 2800 shows an overview of the components of FIG. 27 that have been clamped together.

Clamping plate 2802 clamps together molded flow channel component 2302 over a nanopore array chip. Clamping plate 2802 may be fastened and clamped to circuit board 2702 via screws or other coupling mechanisms. Clamping plate 2802 includes holes to accommodate and allow inlet 2312 and outlet 2314 to pass through clamping plate 2802. Clamping plate 2802 clamps the molded flow channel component to the nanopore array chip to provide the compression required to seal and couple them together in creating a flow channel/chamber without the use of adhesives and/or permanent/physical bonding to couple together the molded flow channel component to the nanopore array chip. Spring contact wire component 2704 is not shown to simplify the diagram but exists in the embodiment under clamping plate 2802. Clamping plate 2802 also secures the spring contact wire component to the counter electrode of the molded flow channel component via compression.

View 2801 shows a cutaway view of the embodiment shown in view 2800. Clamping plate 2802 is secured to circuit board 2702 and clamps together nanopore array chip 2804 with counter electrode portion 2306 and molded portion 2304 of molded flow channel component 2302. The gap between counter electrode portion 2306 and nanopore array chip 2804 is a part of a flow chamber/channel that holds and directs the fluids to traverse over different sensors of nanopore array chip 2804. The clamping force/pressure seals contact between molded portion 2304 and nanopore array chip 2804. In some embodiments, the material of molded portion 2304 is compliant to provide the seal under clamping force/pressure.

Figure 29:
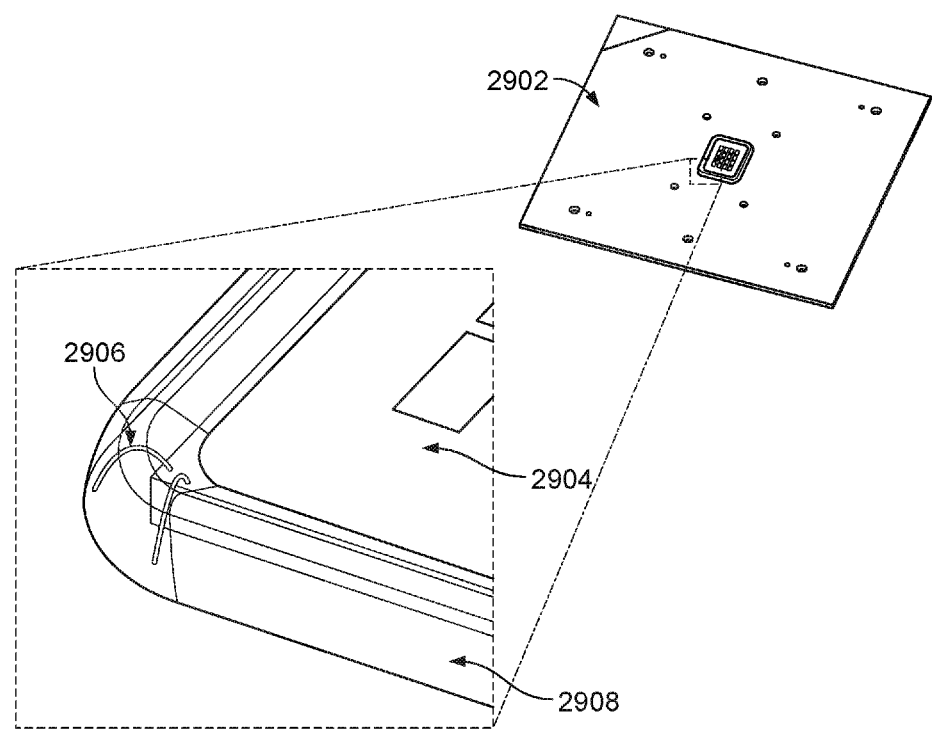
FIG. 29 is a diagram illustrating an embodiment of encapsulated wire bonds.

FIG. 29 is a diagram illustrating an embodiment of encapsulated wire bonds. Wire bonds 2906 electrically connect nanopore based sequencing chip 2904 to circuit board 2902. Wire bonds 2906 are protected by encapsulant 2908. Although only two wire bonds have been shown to simplify the diagram, other wire bonds 2906 all around the perimeter of chip 2904 may be utilized to electrically connect chip 2904 to circuit board 2902. In order to protect wire bonds 2906 from damage and wetting, encapsulant 2908 (e.g., adhesive) is utilized to encapsulate wire bonds 2906 by applying a ring of encapsulant around the perimeter of chip 2904. In some embodiments, encapsulant 2908 is the encapsulant shown as surrounding a nanopore chip in other figures. However, the applied encapsulant cannot encroach on portions of the chip where one or more flow channel components are to be coupled to the chip.

Thus care must be taken to minimize the encroachment of the encapsulant onto the surface of the chip in order to maximize the area available on the chip surface for coupling the one or more flow channel components onto the chip. In various embodiments, the one or more flow channel components may be coupled to the chip surface by room temperature bonding, adhesive bonding, and/or compression bonding. During manufacturing, two distinct steps may need to be performed—first, encapsulating the wire bonds with careful attention paid to preventing undesired encroachment of the encapsulant onto the chip and then coupling and sealing the one or more flow channel components onto the chip.

Figure 30:
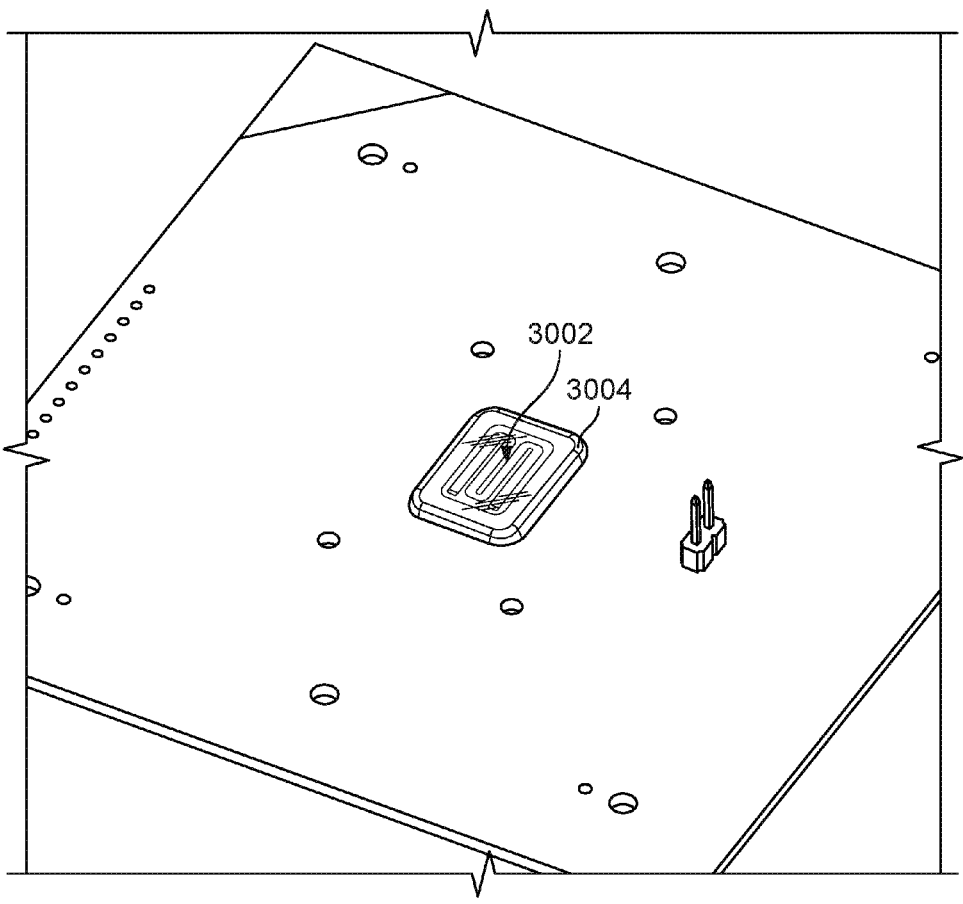
FIG. 30 is a diagram illustrating an embodiment of encapsulating wire bonds together with one or more flow channel components in a single manufacturing step.

FIG. 30 is a diagram illustrating an embodiment of encapsulating wire bonds together with one or more flow channel components in a single manufacturing step. For example, rather than encapsulating wire bonds between a nanopore chip and a circuit board in a separate step from securing one or more flow channel components to the nanopore chip, a single application of encapsulant 3004 is utilized to both encapsulate the wire bonds and couple/secure the one or more flow channel components to the chip. In some embodiments, without first encapsulating wire bonds, flow channel component 3002 is placed on the nanopore chip. Then, a single application of encapsulant (e.g., adhesive) is applied to simultaneously encapsulate the wire bonds and seal the perimeter of flow channel component 3002 to the nanopore based sequencing chip. By combining two manufacturing steps into one encapsulation step, manufacturing becomes more efficient and simplified. Additionally, the chip encroachment restriction on the application of the encapsulant is eliminated because the flow channel component is already placed on the chip and limits the flow of the encapsulant on undesired portions of the chip. Examples of flow channel component 3002 include various components placed on a nanopore cell to form a chamber/flow channel over the sensors of the chip. For example, various gaskets, plates, and reference electrodes described in various embodiments herein may be included in flow channel component 3002. In some embodiments, flow channel component 3002 includes molded flow channel component 2302 of FIG. 23.

Although the foregoing embodiments have been described in some detail for purposes of clarity of understanding, the invention is not limited to the details provided.

There are many alternative ways of implementing the invention. The disclosed embodiments are illustrative and not restrictive.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A nanopore based sequencing system, the system comprising:

a nanopore sensor array comprising a plurality of nanopore sensors, each nanopore sensor comprising a cell and a working electrode, wherein the nanopore sensor array is fabricated on a sequencing chip, wherein the sequencing chip is electrically connected to a printed circuit board with a plurality of wire bonds, wherein the wire bonds are covered by an encapsulant configured to prevent the wire bonds from coming into contact with liquids;

a counter electrode;

a flow channel disposed over the nanopore sensor array;

an inlet configured to deliver the fluid into the flow channel, wherein the inlet is located proximate a first side of the nanopore sensor array; and an outlet configured to deliver fluid out of the flow channel, wherein the outlet is located proximate a second side of the nanopore sensor array, wherein the first side is opposite the second side.

2. The nanopore based sequencing system of claim 1, wherein the nanopore sensor array comprises one million nanopore sensors.

3. The nanopore based sequencing system of claim 1, wherein the cell is configured to support a membrane and a nanopore disposed in the membrane.

4. The nanopore based sequencing system of claim 3, wherein the nanopore is a protein nanopore.

5. The nanopore based sequencing system of claim 4, wherein the protein nanopore is attached to a polymerase.

6. The nanopore based sequencing system of claim 5, wherein the polymerase is associated with a nucleic acid molecule to be sequenced.

7. The nanopore based sequencing system of claim 6, wherein the nucleic acid molecule is circular.

8. The nanopore based sequencing system of claim 1, wherein the nanopore sensors are organized into a plurality of sensor banks.

9. The nanopore based sequencing system of claim 1, further comprising a fan-out plenum in fluid communication with the inlet, the fan-out plenum configured to receive fluid from the inlet and dispense the fluid outwardly into the flow channel.

10. The nanopore based sequencing system of claim 9, further comprising a reverse fan-out plenum in fluid communication with the outlet, the reverse fan-out plenum configured to receive fluid from the fluid channel and direct the fluid to the outlet.

11. The nanopore based sequencing system of claim 1, wherein the encapsulant is an adhesive.

12. The nanopore based sequencing system of claim 1, wherein the adhesive is configured to seal the flow channel over the sensor array and to the printed circuit board.

13. A nanopore based sequencing system, the system comprising:

a nanopore sensor array comprising a plurality of nanopore sensors, each nanopore sensor comprising a cell and a working electrode, wherein the cell is configured to support a membrane and a nanopore disposed in the membrane, wherein the nanopore is attached to a polymerase, wherein the polymerase is associated with a nucleic acid molecule to be sequenced, wherein the nucleic acid molecule is circular, wherein the nanopore sensor array is fabricated on a sequencing chip, wherein the sequencing chip is electrically connected to a printed circuit board with a plurality of wire bonds, wherein the wire bonds are covered by an encapsulant configured to prevent the wire bonds from coming into contact with liquids;

a counter electrode;

a flow channel disposed over the nanopore sensor array;

an inlet configured to deliver the fluid into the flow channel, wherein the inlet is located proximate a first side of the nanopore sensor array; and an outlet configured to deliver fluid out of the flow channel, wherein the outlet is located proximate a second side of the nanopore sensor array, wherein the first side is opposite the second side.

14. The nanopore based sequencing system of claim 13, wherein the nanopore sensor array comprises one million nanopore sensors.

15. The nanopore based sequencing system of claim 13, wherein the nanopore sensors are organized into a plurality of sensor banks.

16. The nanopore based sequencing system of claim 13, further comprising a fan-out plenum in fluid communication with the inlet, the fan-out plenum configured to receive fluid from the inlet and dispense the fluid outwardly into the flow channel.

17. The nanopore based sequencing system of claim 16, further comprising a reverse fan-out plenum in fluid communication with the outlet, the reverse fan-out plenum configured to receive fluid from the fluid channel and direct the fluid to the outlet.

18. The nanopore based sequencing system of claim 14, wherein the encapsulant is an adhesive that is also configured to seal the flow channel over the sensor array and to the printed circuit board.

* * * * *